United States Patent
Hong et al.

(10) Patent No.: US 10,208,097 B2
(45) Date of Patent: Feb. 19, 2019

(54) METHOD FOR TREATING VASCULAR STENOSIS OR OCCLUSIVE DISEASE DUE TO THROMBI BY ADMINISTERING A SAXATILIN-FC FUSION PROTEIN

(71) Applicant: INDUSTRY-ACADEMIC COOPERATION FOUNDATION, YONSEI UNIVERSITY, Seoul (KR)

(72) Inventors: Sung Yu Hong, Seoul (KR); Ji Hoe Heo, Seoul (KR); Il Kwon, Gyeonggi-do (KR); Dong Ik Kim, Seoul (KR); Yang Soo Jang, Seoul (KR); Young Dae Kim, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 15/672,015

(22) Filed: Aug. 8, 2017

(65) Prior Publication Data

US 2018/0057549 A1    Mar. 1, 2018

Related U.S. Application Data

(62) Division of application No. 14/908,906, filed as application No. PCT/KR2014/007013 on Jul. 30, 2014, now abandoned.

(30) Foreign Application Priority Data

Jul. 30, 2013  (KR) .......................... 10-2013-0090468
Jul. 30, 2014  (KR) .......................... 10-2014-0097461

(51) Int. Cl.
C07K 14/46      (2006.01)
A61K 38/00      (2006.01)
C12N 9/64       (2006.01)

(52) U.S. Cl.
CPC ............ *C07K 14/46* (2013.01); *C12N 9/6489* (2013.01); *A61K 38/00* (2013.01); *C07K 2319/30* (2013.01)

(58) Field of Classification Search
CPC .. C07K 14/46; C07K 2319/30; C12N 9/6489; A61K 38/00
See application file for complete search history.

(56) References Cited

U.S. PATENT DOCUMENTS

| | | | |
|---|---|---|---|
| 7,033,788 B2 | 4/2006 | Chung et al. | 435/69.1 |
| 8,183,201 B2 | 5/2012 | Chuang et al. | 514/1.1 |
| 2009/0305301 A1 | 12/2009 | Mirshahi et al. | 435/7.1 |
| 2013/0316951 A1 | 11/2013 | Heo et al. | 514/13.9 |

FOREIGN PATENT DOCUMENTS

| | | | |
|---|---|---|---|
| JP | 2003-523768 A | 8/2003 | |
| JP | 2010-514444 A | 5/2010 | |
| KR | 10-2009-0036908 | 4/2009 | ............. A61K 38/17 |
| KR | 10-2009-0108049 | 10/2009 | ............. A61K 38/16 |
| KR | 10-2012-0061036 | 6/2012 | ............. A61K 38/06 |
| WO | WO 1994/022494 | 10/1994 | ............. A61K 51/04 |
| WO | WO-01/62905 A2 | 8/2001 | |
| WO | WO-01/62905 A3 | 3/2002 | |
| WO | WO-2004/078137 A2 | 9/2004 | |
| WO | WO-2004/078137 A3 | 2/2006 | |
| WO | WO-2012/060607 A2 | 5/2012 | |

OTHER PUBLICATIONS

Hong., et al., (2002). "Snake venom disintegrin, saxatilin, inhibits platelet aggregation, human umbilical vein endothelial cell proliferation, and smooth muscle cell migration." *Thromb. Res.*, 105(1):79-86.
Hong., et al., (2002). "Structural and functional significance of disulfide bonds in saxatilin, a 7.7 kda disintegrin." *Biochem. Biophys. Res. Commun.*, 293(1):530-536.
Jang et al., (2007). Saxatilin, a snake venom disintegrin, regulate platelet activation associated with human vascular endothelial cell migration and invasion. *J. Vasc. Res.*, 44(2):129-137.
Jing (2011). "Inhibition of ovarian cancer by rgd-p125a-endostatin-fc fusion proteins." *Int. J. Cancer*, 129(3):751-761.
International Search Report (ISR) dated Nov. 3, 2014 in PCT/KR2014/007013 published as WO 2015/016616 with English Translation.
Office Action (Non-Final Rejection) dated Feb. 8, 2017 issued in U.S. Appl. No. 14/908,906, which is the parent application of this present application.
Office Action from corresponding Japanese Patent Application No. 2016-531527, dated Mar. 14, 2018, and it's English translation.
Extended European Search Report from corresponding European Patent Application No. 14831205.1, dated Mar. 10, 2018.

*Primary Examiner* — Robert S Landsman
(74) *Attorney, Agent, or Firm* — Harness, Dickey & Pierce, P.L.C.

(57) ABSTRACT

The present invention relates to a saxatilin derivative having an increased half life and a use thereof. The saxatilin derivative of the present invention has thrombolytic ability similar to that of saxatilin, which is the mother protein, a remarkably increased protein half life, and efficiently dissolves, for long period of time, blood clots already formed in blood vessels of an animal model with a $FeCl_3$-induced carotid by using the same. Therefore, a composition containing, as an active ingredient, the saxatilin derivative of the present invention does not cause reocclusion after penetration and effectively opens to microvessels, and is thus very useful for treating angiostenosis or occlusive diseases (for example, cerebrovascular diseases, cardiovascular diseases, arteriosclerotic vascular diseases, coronary artery diseases, and peripheral vascular diseases).

13 Claims, 12 Drawing Sheets

Specification includes a Sequence Listing.

SEQUENCE LISTING

```
<160> NUMBER OF SEQ ID NOS: 7

<210> SEQ ID NO 1
<211> LENGTH: 219
<212> TYPE: DNA
<213> ORGANISM: Gloydius halys

<400> SEQUENCE: 1
gaggccggag aagaatgtga ctgtggcgct cctgcaaatc cgtgctgcga tgctgcaacc      60
tgtaaactga gaccaggggc gcagtgtgca gaaggactgt gttgtgacca gtgcagattt     120
atgaaagaag gaacaatatg ccggatggca aggggtgatg acatggatga ttactgcaat     180
ggcatatctg ctggctgtcc cagaaatccc ttccatgcc                            219

<210> SEQ ID NO 2
<211> LENGTH: 73
<212> TYPE: PRT
<213> ORGANISM: Gloydius halys

<400> SEQUENCE: 2

Glu Ala Gly Glu Glu Cys Asp Cys Gly Ala Pro Ala Asn Pro Cys Cys
1               5                   10                  15

Asp Ala Ala Thr Cys Lys Leu Arg Pro Gly Ala Gln Cys Ala Glu Gly
            20                  25                  30

Leu Cys Cys Asp Gln Cys Arg Phe Met Lys Glu Gly Thr Ile Cys Arg
        35                  40                  45

Met Ala Arg Gly Asp Asp Met Asp Asp Tyr Cys Asn Gly Ile Ser Ala
    50                  55                  60

Gly Cys Pro Arg Asn Pro Phe His Ala
65                  70

<210> SEQ ID NO 3
<211> LENGTH: 957
<212> TYPE: DNA
<213> ORGANISM: Artificial Sequence
<220> FEATURE:
<223> OTHER INFORMATION: Fc-saxatilin fusion protein

<400> SEQUENCE: 3
gacaaaactc acacatgccc accgtgccca gcacctgaac tcctgggggg accgtcagtc      60
ttcctctttc ccccaaaacc caaggacacc ctcatgatct cccggacccc tgaggtcaca     120
tgcgtggtgg tggacgtgag ccacgaagac cctgaggtca agttcaactg gtacgtggac     180
ggcgtggagg tgcataatgc caagacaaag ccgcgggagg agcagtacaa cagcacgtac     240
cgtgtggtca gcgtcctcac cgtcctgcac caggactggc tgaatggcaa ggagtacaag     300
```

| | |
|---|---:|
| tgcaaggtct ccaacaaagc cctcccagcc cccatcgaga aaaccatctc caaagccaaa | 360 |
| gggcagcccc gagaaccaca ggtgtacacc ctgcccccat cccgggagga gatgaccaag | 420 |
| aaccaggtca gcctgacctg cctggtcaaa ggcttctatc ccagcgacat cgccgtggag | 480 |
| tgggagagca atgggcagcc ggagaacaac tacaagacca cgcctcccgt gctggactcc | 540 |
| gacggctcct tcttcctcta cagcaagctc accgtggaca agagcaggtg gcagcagggg | 600 |
| aacgtcttct catgctccgt gatgcatgag gctctgcaca accactacac gcagaagagc | 660 |
| ctctccctgt ctccgggtaa actggtgccg cgcggcagcc atcatcatca tcaccacgga | 720 |
| tccggggccg tggggccgga ggccggagaa gaatgtgact gtggcgctcc tgcaaatccg | 780 |
| tgctgcgatg ctgcaacctg taaactgaga ccaggggcgc agtgtgcaga aggactgtgt | 840 |
| tgtgaccagt gcagatttat gaagaagga acaatatgcc ggatggcaag gggtgatgac | 900 |
| atggatgatt actgcaatgg catatctgct ggctgtccca gaaatccctt ccatgcc | 957 |

<210> SEQ ID NO 4
<211> LENGTH: 319
<212> TYPE: PRT
<213> ORGANISM: Artificial Sequence
<220> FEATURE:
<223> OTHER INFORMATION: Fc-saxatilin fusion protein

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val

```
Pro Ala Asn Pro Cys Cys Asp Ala Ala Thr Cys Lys Leu Arg Pro Gly
            260                 265                 270

Ala Gln Cys Ala Glu Gly Leu Cys Cys Asp Gln Cys Arg Phe Met Lys
        275                 280                 285

Glu Gly Thr Ile Cys Arg Met Ala Arg Gly Asp Asp Met Asp Asp Tyr
    290                 295                 300

Cys Asn Gly Ile Ser Ala Gly Cys Pro Arg Asn Pro Phe His Ala
305                 310                 315
```

<210> SEQ ID NO 5
<211> LENGTH: 963
<212> TYPE: DNA
<213> ORGANISM: Artificial Sequence
<220> FEATURE:
<223> OTHER INFORMATION: saxatilin-Fc fusion protein

<400> SEQUENCE: 5

```
gaggccggag aagaatgtga ctgtggcgct cctgcaaatc cgtgctgcga tgctgcaacc     60
tgtaaactga gaccagggggc gcagtgtgca aaggactgt gttgtgacca gtgcagattt    120
atgaaagaag gaacaatatg ccggatggca agggtgatg acatggatga ttactgcaat    180
ggcatatctg ctggctgtcc cagaaatccc ttccatgcct ggccgcgtc ggccgctagc    240
catcatcatc atcaccacag cggcctggtg ccgcgcggca cgacaaaac tcacacatgc    300
ccaccgtgcc cagcacctga actcctgggg ggaccgtcag tcttcctctt ccccccaaaa    360
cccaaggaca cctcatgat ctcccggacc cctgaggtca catgcgtggt ggtggacgtg    420
agccacgaag accctgaggt caagttcaac tggtacgtgg acggcgtgga ggtgcataat    480
gccaagacaa agccgcggga ggagcagtac aacagcacgt accgtgtggt cagcgtcctc    540
accgtcctgc accaggactg gctgaatggc aaggagtaca agtgcaaggt ctccaacaaa    600
gccctcccag cccccatcga gaaaaccatc tccaaagcca aagggcagcc ccgagaacca    660
caggtgtaca ccctgcccc atcccgggat gagctgacca agaaccaggt cagcctgacc    720
tgcctggtca aaggcttcta tcccagcgac atcgccgtgg agtgggagag caatgggcag    780
ccggagaaca actacaagac cacgcctccc gtgctggact ccgacggctc cttcttcctc    840
tacagcaagc tcaccgtgga caagagcagg tggcagcagg ggaacgtctt ctcatgctcc    900
gtgatgcatg aggctctgca caaccactac acgcagaaga gcctctccct gtctccgggt    960
aaa                                                                  963
```

<210> SEQ ID NO 6
<211> LENGTH: 321
<212> TYPE: PRT
<213> ORGANISM: Artificial Sequence
<220> FEATURE:
<223> OTHER INFORMATION: saxatilin-Fc fusion protein

<400> SEQUENCE: 6

```
Glu Ala Gly Glu Glu Cys Asp Cys Gly Ala Pro Ala Asn Pro Cys Cys
1               5                   10                  15

Asp Ala Ala Thr Cys Lys Leu Arg Pro Gly

Gly Cys Pro Arg Asn Pro Phe His Ala Leu Ala Ser Ala Ala Ser
65                  70                  75                  80

His His His His His Ser Gly Leu Val Pro Arg Gly Ser Asp Lys
                85                  90                  95

Thr His Thr Cys Pro Pro Cys Pro Ala Pro Glu Leu Leu Gly Gly Pro
                100                 105                 110

Ser Val Phe Leu Phe Pro Pro Lys Pro Lys Asp Thr Leu Met Ile Ser
            115                 120                 125

Arg Thr Pro Glu Val Thr Cys Val Val Val Asp Val Ser His Glu Asp
        130                 135                 140

Pro Glu Val Lys Phe Asn Trp Tyr Val Asp Gly Val Glu Val His Asn
145                 150                 155                 160

Ala Lys Thr Lys Pro Arg Glu Glu Gln Tyr Asn Ser Thr Tyr Arg Val
                165                 170                 175

Val Ser Val Leu Thr Val Leu His Gln Asp Trp Leu Asn Gly Lys Glu
            180                 185                 190

Tyr Lys Cys Lys Val Ser Asn Lys Ala Leu Pro Ala Pro Ile Glu Lys
        195                 200                 205

Thr Ile Ser Lys Ala Lys Gly Gln Pro Arg Glu Pro Gln Val Tyr Thr
    210                 215                 220

Leu Pro Pro Ser Arg Asp Glu Leu Thr Lys Asn Gln Val Ser Leu Thr
225                 230                 235                 240

Cys Leu Val Lys Gly Phe Tyr Pro Ser Asp Ile Ala Val Glu Trp Glu
                245                 250                 255

Ser Asn Gly Gln Pro Glu Asn Asn Tyr Lys Thr Thr Pro Pro Val Leu
            260                 265                 270

Asp Ser Asp Gly Ser Phe Phe Leu Tyr Ser Lys Leu Thr Val Asp Lys
        275                 280                 285

Ser Arg Trp Gln Gln Gly Asn Val Phe Ser Cys Ser Val Met His Glu
    290                 295                 300

Ala Leu His Asn His Tyr Thr Gln Lys Ser Leu Ser Leu Ser Pro Gly
305                 310                 315                 320

Lys

<210> SEQ ID NO 7
<211> LENGTH: 227
<212> TYPE: PRT
<213> ORGANISM: Artificial Sequence
<220> FEATURE:
<223> OTHER INFORMATION: IgG1 Fc fragment

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile

-continued

```
                100                 105                 110
Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
            210                 215                 220

Pro Gly Lys
225
```

METHOD FOR TREATING VASCULAR STENOSIS OR OCCLUSIVE DISEASE DUE TO THROMBI BY ADMINISTERING A SAXATILIN-FC FUSION PROTEIN

CROSS-REFERENCE RELATED APPLICATIONS

This application is a divisional application of U.S. Ser. No. 14/908,906, filed on 29 Jan. 2016 (now abandoned), which claims benefit of PCT Application no. PCT/KR2014/007013, filed on 30 Jul. 2014, which claims benefit of Korean Patent Application 10-2014-0097461, filed on 30 Jul. 2014 and Korean Patent Application 10-2013-0090468, filed on 30 Jul. 2013. The entire disclosure of the applications identified in this paragraph is incorporated herein by reference.

FIELD

The present invention was made with the support of the Ministry of Health and Welfare, Republic of Korea, under Project No. A085136, which was conducted in the program titled "Leading Characterization Research and Development Business" in the project named "Leading Cerebro-cardiovascular Diseases Fusion Research Business Consortium", by the Industry-Academic Cooperation Foundation, YONSEI University, under management of the Korea Health Industry Development Institute, from 1 Dec. 2012 to 30 Nov. 2013.

The present invention relates to a saxatilin derivative having an increased half-life and a use thereof.

BACKGROUND

Most strokes are caused by thromboembolic occlusion in major or smaller intracerebral arteries (Wardlaw, Murray et al. 2009). In ischemic stroke, rapid thrombolysis is the only established therapeutic option to suppress the onset of unavoidable complete infarction (1995; Choi and Bateman et al. 2006). Treatment through the intravenous administration of recombinant tissue plasminogen activator (r-tPA) is currently the only approved therapy for ischemic stroke, which can be made within 4.5 hours after the onset of ischemic stroke (Caplan, Mohr et al. 1997; and Lopez-Yunez, Bruno et al. 2001). However, more than half the patients failed to achieve successful recanalization after thrombolytic treatment (Rha and Saver 2007; and Lee et al. Stroke 2007; 38:192-193]. Even if occluded arteries are successfully recanalized by the thrombolytic treatment, these benefits are again degraded due to the risks of reperfusion injury (Hallenbeck and Dutka 1990), intracerebral hemorrhage (Adams, Adams et al. 2005), and reocclusion (Heo, Lee et al 2003). In addition, rt-PA was reported to have neurotoxicity (Chen and Strickland 1997; Wang, Tsirka et al. 1998; Nicole, Docagne et al. 2001; Yepes, Sandkvist et al. 2002; and Matys and Strickland 2003).

Although the recanalization strategy has proven its efficacy, it caused limited applicability and potential adverse effects, and thus there have been efforts to develop new thrombolytic agents having better effects than rt-PA. These efforts include variants of t-PA, plasminogen activators derived from animal sources, and microplasmin. The above-cited drugs have the following purposes: (a) enhancing fibrin specificity; (2) extending plasma half-life; (3) reducing inhibitory ability by plasminogen activator inhibitor-1; and (d) avoiding neurotoxicity. Several drugs have completed clinical trials, and some drugs are being studied for their efficacy. These drugs target fibrin in the thrombi, and thrombolytic agents, such as rt-PT and urokinase, correspond to these drugs. However, the thrombi are formed by a platelet-fibrinogen interaction. Thrombin, leukocytes, and erythrocytes are also components of the thrombus. The resistance of the thrombi to the thrombolytic agents targeting fibrin is one of the main causes of low recanalization rates in stroke patients, which may occur more commonly in occlusion by platelet-rich thrombi. In this regard, the treatment targeting platelets may be an option or additive to the treatment targeting fibrin for improved thrombolytic efficacy.

Platelet glycoprotein (GP) IIb/IIIa, a member of the integrin family, exists on the surface of the platelet membrane at high density (Shattil and Ginsberg 1997). The GPIIb/IIIa receptor mediates the final stage of the platelet aggregation pathway by specifically binding to fibrinogen (Phillips, Charo et al. 1988). Therefore, targeting the platelet GPIIb/IIIa receptor has been the mainstay for the development of drugs acting on the platelets. Many platelet GPIIb/IIIa antagonists have been developed, which include the Fab fragment of a human-mouse chimeric antibody against GP IIb/IIIa (abciximab), nonpeptide analogues of RGD peptides (tirofiban and lamifiban), and cyclic heptapeptide disintegrin containing KGD motif (eptifibatide) (Seitz, Meisel et al. 2004; Abou-Chebl, Bajzer et al. 2005; and Eckert, Koch et al. 2005). These GPIIb/IIIa antagonists have been effective for patients with unstable angina, acute myocardial infarction, and percutaneous treanfemoral coronary angioplasty (PTCA) and patients receiving stent. In stroke, abciximab failed to show efficacy in patients who were treated 5 to 6 hours after the symptom onset (Adams, Effron et al. 2008). However, GPIIb/IIIa antagonists lyse the thrombi in stroke patients with reocclusion, and are effective for selected patients (Heo, Lee et al. 2003; Seitz, Hamzavi et al. 2003; Seitz, Meisel et al. 2004; Eckert, Koch et al. 2005; and Chen, Mo et al. 2007).

Saxatilin, which is a novel disintegrin that is purified and cloned from Korean snake venom, has the tripeptide sequence Arg-Gly-Asp (RGD), which is a recognition site of disintegrin to the platelet GPIIb/IIIa receptor (Hong, Koh et al. 2002; and Hong, Sohn et al. 2002). It has been known that saxatilin has strong inhibitory effects on platelet aggregation (Hong, Koh et al. 2002) and platelet activation (Jang, Jeon et al. 2007), and thus interrupts the generation of thrombus.

Throughout the entire specification, many papers and patent documents are referenced and their citations are represented. The disclosure of the cited papers and patent documents are entirely incorporated by reference into the present specification and the level of the technical field within which the present invention falls, and the details of the present invention are explained more clearly.

DETAILED DESCRIPTION

Technical Problem

The present inventors have endeavored to develop a thrombolytic agent, which can recanalize a partially or completely occluded blood vessel by effectively suppressing the generation of thrombi or lysing the already generated thrombi. As a result, the present inventors validated that a recombinant protein (or a saxatilin derivative), which is composed of disintegrin, specifically, saxatilin, derived from Korean snake venom, and an immunoglobulin Fc fragment, has similar thrombolytic activity to the saxatilin protein as well as a significantly increased protein half-life, enables very efficient lysis of the thrombi, which were already generated in the blood vessel in FeCl₃-induced carotid artery animal models, and can maintain its activity for a longer time than the parent protein, saxatilin, and thus the present inventors completed the present invention.

Accordingly, an aspect of the present invention is to provide a saxatilin derivative.

Another aspect of the present invention is to provide a nucleotide sequence encoding the saxatilin derivative.

Still another aspect of the present invention is to provide a recombinant vector including the nucleotide sequence.

Still another aspect of the present invention is to provide cells transfected with the recombinant vector.

Still another aspect of the present invention is to provide a composition for thrombolysis.

Still another aspect of the present invention is to provide a pharmaceutical composition for preventing or treating stenosis of blood vessel or occlusive disease.

Still another aspect of the present invention is to provide a method for preventing or treating stenosis of blood vessel or occlusive disease.

Still another aspect of the present invention is to provide a use of a saxatilin derivative for preventing or treating stenosis of blood vessel or occlusive disease.

Other purposes and advantages of the present disclosure will become more obvious with the following detailed description of the invention, claims, and drawings.

Technical Solution

In accordance with an aspect of the present invention, there is provided a saxatilin derivative including saxatilin, which is composed of the amino acid sequence of SEQ ID NO: 2, conjugated to an immunoglobulin Fc region.

In accordance with another aspect of the present invention, there is provided a nucleotide sequence encoding the foregoing saxatilin derivative.

In accordance with another aspect of the present invention, there is provided a recombinant vector, including: (a) the foregoing nucleotide sequence; and (b) a promoter operatively linked to the nucleotide sequence.

In accordance with still another aspect of the present invention, there is provided a cell or transformant transinfected with the foregoing recombinant vector.

The present inventors have endeavored to develop a thrombolytic agent, which can recanalize a partially or completely occluded blood vessel by effectively suppressing the generation of thrombi or lysing the already generated thrombi. As a result, the present inventors validated that a recombinant protein (or a saxatilin derivative), which is composed of disintegrin, specifically, saxatilin, derived from Korean snake venom, and an immunoglobulin Fc fragment, has similar thrombolytic activity to that of the saxatilin protein as well as a significantly increased protein half-life, enables very efficient lysis of the thrombi, which were already generated in the blood vessel in FeCl₃-induced carotid artery animal models, and can maintain its activity for a longer time than the parent protein, saxatilin.

The saxatilin derivative of the present invention, which is a fusion protein of saxatilin (SEQ ID NO: 1 and SEQ ID NO: 2) and Fc, is composed of saxatilin, including an amino acid sequence of SEQ ID NO: 2, and an immunoglobulin Fc region. The saxatilin derivative can efficiently break up the thrombus through a principle in which the saxatilin derivative competitively binds to an integrin existing in the thrombus (specifically, glycoprotein (GP) IIb-IIIa on a surface of platelets constituting the thrombus), thereby separating the platelets and the like from constituents of the thrombus, such as fibrinogen.

According to a certain embodiment of the present invention, the saxatilin derivative of the present invention has similar thrombolytic activity to saxatilin, which is the parent protein thereof.

In an embodiment of the present invention, the saxatilin derivative of the present invention has an $IC_{50}$ value of 100-500 nM, and preferably 100-250 nM, with respect to platelet aggregation.

Specifically, the $IC_{50}$ values of saxatilin as the parent protein, Fc-saxatilin, and saxatilin-Fc, were 150 nM, 196 nM, and 362 nM, respectively (see: FIG. 4). As used herein, the term "$IC_{50}$ value (half maximal inhibitory concentration)" refers to an indicator that evaluates the efficacy of a compound inhibiting biological or biochemical activity, and offers a quantitative concentration measurement value at which a particular drug or other substances (e.g., a saxatilin derivative of the present invention) inhibit a given biological process (e.g., thrombolysis) or components of the process (e.g., an enzyme or cell receptor) by half. It is commonly used as a measure of antagonist drug potency in pharmacological research. Meanwhile, thrombolytic activity may be measured by using various methods known in the art: for example, fibrin plate assay (Astrup A and Mullertz S., The fibrin plate method for estimating fibrinolytic activity. *Arch Biochem Biophys* 40: 346-351(1952)); the detection of D-dimer showing the breakage of platelets (U.S. Patent Publication No. US 2009/0305301 A1); the use of radioisotope (PCT Patent Publication No. WO 1994/022494); the measurement of thrombus weight in the blood vessel; and the measurement of turbidity of powder released after thrombolysis, but are not limited thereto.

In an embodiment of the present invention, the saxatilin derivative of the present invention has a binding affinity (dissociation constant (Kd)) of $1 \times 10^{-8}$ to $1 \times 10^{-10}$ M to integrin $\alpha_M\beta_2$ existing in neutrophils.

In an embodiment of the present invention, the saxatilin derivative of the present invention has a binding affinity (dissociation constant (Kd)) of $1 \times 10^{-8}$ to $1 \times 10^{-10}$ M to integrin $\alpha_L\beta_2$ existing in neutrophils.

According to a certain embodiment of the present invention, the throughput of the saxatilin derivative of the present invention is 1-20 mg/kg, more specifically, 3-15 mg/kg, and most specifically, 5-10 mg/kg. According to the present invention, the saxatilin derivative of the present invention showed an effect on the recanalization of the completely occluded blood vessel at a small dose (see FIG. 6). The treatment with 130 nmol/kg saxatilin, Fc-saxatilin, or saxatilin-Fc showed a blood flow recovery effect of about 30% in the recanalization of the completely occluded blood vessel. Further, the saxatilin treatment group showed reocclusion at approximately 90 min, but the Fc-saxatilin or saxatilin-Fc treatment group showed a continuous recanalization effect.

According to a certain embodiment of the present invention, the saxatilin derivative of the present invention may be administered orally or parentally, specifically parentally, and examples of the parental administration may include bolus injection, intravenous injection, intra-arterial injection, intramuscular injection, intraperitoneal injection, topical administration, dermal administration, etc., and most preferably, the saxatilin derivative of the present invention may be administered by bolus injection.

In addition, the drug having a vascular recanalization effect (e.g., the saxatilin derivative of the present invention), preferably, has a suitable retention time, and specifically, a retention time of approximately 10 min is clinically most suitable and effective.

According to a certain embodiment of the present invention, the immunoglobulin Fc region contained in the saxatilin derivative of the present invention is conjugated to the N-terminal or C-terminal of saxatilin, and more specifically, conjugated to the N-terminal of saxatilin.

According to a certain embodiment of the present invention, the saxatilin derivative of the present invention further includes a leader sequence at the N-terminal thereof.

Conventionally, the fusion protein having the immunoglobulin Fc region binding to a target protein exhibits lower activity or a smaller half-life increase effect when compared with the parent protein. Whereas, the saxatilin derivative of the present invention not only had similar thrombolytic activity to the parent protein, but also showed a significantly increased half-life compared with the parent protein (see FIGS. 5A to 5C). Specifically, the half-lives of Fc-saxatilin and saxatilin-Fc of the present invention were 8.6 min and 12.5 min, respectively, which were much longer than the half-life (2.0 min) of the parent protein saxatilin.

According to a certain embodiment of the present invention, the saxatilin derivative of the present invention has a half-life, which is increased by at least 4-fold, more specifically, about 4- to 6.5-fold, when compared with the parent protein saxatilin.

As used herein, the term "Fc region" refers to the carboxyl terminal portion of an immunoglobulin chain constant region, specifically, an immunoglobulin heavy chain constant region or a part thereof. For example, the immunoglobulin Fc region that may be used in the preparation of the saxatilin derivative of the present invention, may include: (a) CH1 domain, CH2 domain, and CH3 domain; (b) CH1 domain and CH2 domain; (c) CH1 domain and CH3 domain; (d) CH2 domain and CH3 domain; or (e) a combination of two or more domains and a immunoglobulin hinge region.

According to a certain embodiment of the present invention, the immunoglobulin Fc region that may be used in the preparation of the saxatilin derivative of the present invention includes a human immunoglobulin Fc region (GenBank Accession No., CAA49866.1) and fragments thereof (e.g., SEQ ID NO: 7).

Besides the human immunoglobulin Fc region, amino acid sequences, which are encoded by the nucleotide sequences disclosed in GenBank and/or EMBL database, for example, other immunoglobulin Fc regions including AF045536.1 (*Macaca fuscicularis*), AF045537.1 (*Macaca mulatta*), AB016710 (*Felix catus*), K00752 (*Oryctolagus cuniculus*), U03780 (*Sus scrofa*), Z48947 (*Camelus dromedarius*), X62916 (*Bos taurus*), L07789 (*Mustela vision*), X69797 (*Ovis aries*), U17166 (*Cricetulus migratorius*), X07189 (*Rattus rattus*), AF57619.1 (*Trichosurus vulpecula*) or AF035195 (*Monodelphis domestica*), or fragments thereof may also be used.

Further, the substitution or deletion of the amino acid sequence in the immunoglobulin heavy chain constant region may be used in the preparation of the saxatilin derivative of the present invention. Fc mutants, which are prepared through the substitution or deletion, improve safety, dissolubility, and structural integrity of fusion proteins, and thus are useful in the preparation of optimized fusion proteins.

The present invention provides a nucleotide sequence encoding a fusion protein (SEQ ID NO: 4 or SEQ ID NO: 6) composed of saxatilin of SEQ ID NO: 2 and the immunoglobulin Fc region of SEQ ID NO: 7, which are specifically exemplified as SEQ ID NO: 3 and SEQ ID NO: 5, but are not limited thereto. It would be obvious to a person skilled in the art that any nucleotide sequence that encodes the fusion protein may be used.

In addition, the fusion protein of the present invention may be tagged with various detectable indication tags, and the examples of the tag may include a flag, c-Myc, HA, V5, VSV-G, and HSV, but are not limited thereto. As used herein, the term "tag" refers to a polynucleotide sequence having 3 to 40 amino acid sequences, and gives specific binding affinity to the fusion protein of the present invention, a peptide, a protein ligand (e.g., the fusion protein of the present invention), or a non-peptide ligand. In addition, the tag that may be used in the present invention may include a fluorescent tag, a luminescent tag, and a chromogenic tag.

The saxatilin derivative of the present invention may be mass-produced at low costs by using a recombinant vector including: (a) a nucleotide sequence encoding the saxatilin derivative; and (b) a promoter operatively linked to the nucleotide sequence.

As used herein, the term "promoter" refers to a DNA sequence that regulates the expression of a coding sequence or functional RNA. In the recombinant expression vector of the present invention, a material to be expressed (i.e., saxatilin-Fc-fused protein)-encoding nucleotide sequence is operatively linked to the promoter. As used herein, the term "operatively linked" refers to a functional linkage between a nucleic acid expression regulating sequence (e.g., a promoter sequence, a signal sequence, or an array at the binding site of a transcription control factor) and another nucleic acid sequence, and the regulating sequence regulates the transcription and/or translation of the another nucleic acid sequence.

The vector system of the present invention can be constructed by various methods known in the art, and a specific method thereof is disclosed in Sambrook et al., *Molecular Cloning, A Laboratory Manual*, Cold Spring Harbor Laboratory Press (2001), which is incorporated herein by reference.

In cases where the vector of the present invention uses prokaryotic cells as a host, it generally carries a strong promoter to initiate transcription (e.g., tac promoter, lac promoter, lacUV5 promoter, lpp promoter, $p_L$ promoter, $p_R$ promoter, rac5 promoter, amp promoter, recA promoter, SP6 promoter, trp promoter, or T7 promoter), a ribosome binding site for translation initiation, and a transcription/translation termination sequence. Here, the bacterial replication origin may be selected from replication origins that are well known in the art to be useful in the stable bacterial replication of long DNA inserts, and examples thereof may include ColE1, F-factor, and P1 replicon, but are not limited thereto. As the bacterial selection marker of the present invention, bacterial selection marker genes that are known in the art may be used. For example, examples of the bacterial selection marker gene may include genes that confer resistance to antibiotics, such as ampicillin, kanamycin, tetracycline, Zeocin, neomycin, hygromycin, and chloramphenicol, but are not limited thereto. In cases where *E. coli* is used as a host cell, the promoter and operator region for the tryptophan biosynthesis pathway (Yanofsky, C., J. Bacteriol., 158:1018-1024(1984)) and the leftward promoter from phage λ ($p_L$λ promoter, Herskowitz, I. and Hagen, D., Ann. Rev. Genet., 14:399-445(1980)) may be used as regulating sequences.

In addition, in cases where the recombinant vector of the present invention is applied to eukaryotic cells, the promoter can regulate the transcription of the material to be expressed, of the present invention, and includes promoters derived from mammalian viruses and promoters derived from mammalian cell genomes. Examples thereof may include cytomegalovirus (CMV) promoter, adenovirus late promoter, vaccinia virus 7.5K promoter, SV40 promoter, tk promoter of HSV, RSV promoter, EF1 alpha promoter, metallothionein promoter, beta-actin promoter, a promoter of human IL-2 gene, a promoter of human IFN gene, a promoter of human IL-4 gene, a promoter of human lymphotoxin gene, and a promoter of human GM-CSF gene, but are not limited thereto.

Preferably, the recombinant vector used in the present invention includes a polyadenylation sequence (e.g., bovine growth hormone terminator or SV40-derived polyadenylation sequence).

The delivery of the vector of the present invention into the host cell may be conducted by various methods known in the art. For example, in cases where the host cells are eukaryotic cells, the delivery may be conducted by the $CaCl_2$ method (Cohen, S. N. et al., Proc. Natl. Acac. Sci. USA, 9:2110-2114(1973)), the Hannahan's method (Cohen, S. N. et al., Proc. Natl. Acac. Sci. USA, 9:2110-2114(1973); and Hanahan, D., J. Mol. Biol., 166:557-580(1983)), and an electroporation method (Dower, W. J. et al., Nucleic. Acids Res., 16:6127-6145(1988)). In cases where the host cells are prokaryotic cells, the delivery may be conducted by using transduction, electroporation, lipofection, microinjection, particle bombardment, yeast spheroplast/cell fusion used in YAC, *Agrobacterium*-mediated transformation used in plant cells, or the like.

In addition, the production of animal cells using the recombinant vector of the present invention may be achieved by a gene transfer method that is commonly known in the art. For example, the method includes electroporation, liposome-mediated transfer (Wong, et al., 1980), and retrovirus-mediated transfer (Chen, H. Y., et al., (1990), J. Reprod. Fert. 41:173-182; Kopchick, J. J. et al., (1991) Methods for the introduction of recombinant DNA into chicken embryos. In Transgenic Animals, ed. N. L. First & F. P. Haseltine, pp. 275-293, Boston; Butterworth-Heinemann; Lee, M.-R. and Shuman, R. (1990) Proc. 4th World Congr. Genet. Appl. Livestock Prod. 16, 107-110), but is not limited thereto.

According to a certain embodiment of the present invention, the foregoing transgenic animal cells are mammal-derived cells.

According to a certain embodiment of the present invention, when animal cells with a foreign gene are selected, the foreign gene is a selection marker, and preferably includes an antibiotic-resistant gene. The selection marker that is usable in the present invention may be any gene that confers antibiotic activity to eukaryotic cells, and examples thereof may include neomycin- and kanamycin-resistant genes, but are not limited thereto.

In accordance with another aspect of the present invention, there is provided a composition for thrombolysis, the composition containing: (a) a pharmaceutically effective amount of the foregoing saxatilin derivative; and (b) a pharmaceutically acceptable carrier.

In accordance with still another aspect of the present invention, there is provided a pharmaceutical composition for preventing or treating vascular stenosis or occlusive disease, the pharmaceutical composition containing the foregoing composition for thrombolysis.

Since the composition of the present invention contains the foregoing saxatilin derivative of the present invention as an active ingredient, descriptions of overlapping contents between the two are omitted to avoid excessive complication of the specification due to repetitive descriptions thereof.

The composition of the present invention can be conveniently and efficiently applied to the treatment of a variety of vascular stenosis or occlusive disease by effectively lysing the already generated and agglomerated thrombus. That is, the composition of the present invention can be applied to the treatment of vascular stenosis or occlusive disease through a principle in which the already generated thrombi are lysed to penetrate blood vessels effectively.

As used herein, the term "occlusion" refers to covering the narrowing of blood vessels due to the complete or partial blocking of the blood vessel. The degree of occlusion, recited in the present invention, may be determined based on the measured blood flow. That is, the degree of occlusion is categorized as a partial occlusion or a complete occlusion. The partial occlusion means the reduction of the baseline blood flow to 40-80%, and the complete occlusion means the reduction of baseline blood flow to 100%.

The blood flow in the blood vessel may be measured by the method known in the art, and examples thereof may include ultrasound dilution (Lee K H, Park J Y, Choi S J, Kim J K, Hwang S D, Joh J H, Clinical utility of access blood flow measurement by ultrasound dilution in hemodialysis patients. Korean J Nephrol, 24: 265-273(2005)), doppler ultrasonography (Strauch B, O'Connoll R, Geoly K, Forcasting thrombosis of vascular access with doppler flow imaging. Am J Kidney Dis, 19: 554-557, (1992)), glucose pump test (GPT; Magnasco A, Alloatti S, Martinoli C, Solari P, Glucose pump test: a new method for blood flow measurements. Nephrol Dial Transplant, 17: 2244-2248(2002)), the use of near-infrared (700-1000 nm) (Buunk G, van der Hoeven J G, Meinders A E, A comparison of near-infrared spectroscopy and jugular bulb oximetry in comatose patients resuscitated from a cardiac arrest. Anesthesia, 53: 13-19 (1998)), thermal diffusion blood flow measurement (Ogata N, Fournier J Y, Imhof H G, et al., Thermal diffusion blood flow monitoring during aneurysm surgery. Acta Neurochir (Wien), 138: 726-731(1996)), and the like, but are not limited thereto. According to a certain embodiment of the present invention, the blood flow may be measured by using a doppler ultrasonography using ultrasonic waves.

According to a certain embodiment of the present invention, the animals to which the composition of the present invention is applied are not particularly limited, and may specifically be mammals; more specifically, a human being, a mouse, a rat, a rabbit, a monkey, a pig, a horse, a cow, a sheep, an antelope, a dog, and a cat; and still more specifically, a human and a mouse.

According to a certain embodiment of the present invention, the animal blood vessel includes arteries, veins, and capillaries; more specifically, main arteries, carotid arteries, subclavian arteries, celiac arteries, mesenteric arteries, renal arteries, iliac arteries, arterioles, capillaries, and venulas; and most preferably main arteries and carotid arteries.

Diseases that may be treated by the composition of the present invention include a variety of vascular stenosis or occlusive disease, for example, cerebrovascular disease (CVD), cardiovascular disease, arteriovascular disease, coronary artery disease (CAD), peripheral artery disease (PAD), more specifically, stroke, cerebral infarction, cerebral thrombosis, cerebral embolism, and the like; more specifically, stroke, cerebral infarction, cerebral thrombosis, cerebral embolism, lacunar infarction, acute coronary syndrome, angina, aortic stenosis, myocardial infarction, migraine, bundle branch block, ischemia, acute ischemic arteriovascular event, thrombophlebitis, venous thromboembolism, deep vein thrombosis, pulmonary embolism, peripheral vascular disease, vascular headache, atherosclerosis, vascular spasm, restenosis, restenosis after balloon angioplasty, and vascular occlusion by vasculitis; and most specifically, stroke, cerebral infarction, cerebral thrombosis, cerebral embolism, myocardial infarction.

As used herein, the term "cerebrovascular disease (CVD)" refers to arteriosclerotic vessel disease occurring in the blood vessel, which supplies oxygen-rich blood to the face and brain, and the cerebrovascular diseases generally includes comorbid disease occurring together with CAD and/or peripheral artery disease (PAD), as well as ischemic disease or lack of blood flow. For example, CVD includes ischemic cerebrovascular disease, acute ischemic stroke, ischemic stroke, hemorrhagic stroke, varicose veins, mild cognitive impairment (MCI) or transient ischemic attacks (TIA), but is not limited thereto.

As used herein, the term "cardiovascular disease" or "arteriosclerotic disease" is a generic term used to classify numerous conditions that affect the heart, heart valves, blood, and vasculature, and covers diseases that affect the heart or blood vessels. Specifically, this disease includes metabolic syndromes, syndrome X, atherosclerosis, atherothrombosis, coronary artery disease, stable and unstable angina, stroke, aortic disease, such as aortic stenosis or aortic aneurysm, cerebrovascular disease, peripheral vascular disease, or acute ischemic atherosclerotic events, but is not limited thereto. Especially, the arteriovascular disease means ishemic disease or proischemic disease, rather than non-ishemic disease.

As used herein, the term "coronary artery disease (CAD)" refers to arteriosclerotic vessel disease caused by the hardening and/or narrowing of the artery (coronary artery), which supplies blood to heart muscles, due to atherosclerotic or calcium precipitation. CAD causes a reduction in the blood flow to the heart muscles, such that the heart muscles do not receive a sufficient amount of oxygen, resulting in necrosis. CAD includes acute coronary artery syndrome, myocardial infarction (heart attack), angina (stable and unstable), or atherosclerosis and atherothrombosis, which are caused in blood vessels supplying blood to the heart, but is not limited thereto.

As used herein, the term "peripheral artery disease (PAD)" refers to disease, such as atherosclerosis or atherothrombosis, occurring in parts other than the heart and brain, and generally includes comorbid disease occurring together with CAD.

As used herein, the term "pharmaceutically effective amount" refers to an amount that is sufficient to attain efficacy or activity (that is, thrombolytic activity) of the above-described saxatilin derivative.

The pharmaceutical composition of the present invention contains a pharmaceutically acceptable carrier. The pharmaceutically acceptable carrier contained in the pharmaceutical composition of the present invention is conventionally used for the formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain a lubricant, a wetting agent, a sweetening agent, a flavoring agent, an emulsifier, a suspending agent, a preservative, and the like, in addition to the above ingredients. Suitable pharmaceutically acceptable carriers and preparations are described in detail in *Remington's Pharmaceutical Sciences* (19th ed., 1995).

A suitable dose of the pharmaceutical composition of the present invention may vary depending on various factors, such as the method for formulation, manner of administration, the age, body weight, gender, and morbidity of the patient, diet, time of administration, excretion rate, and response sensitivity. The pharmaceutical composition of the present invention may be administered orally or parentally, and examples of the parental administration may include bolus injection, intravenous injection, subcutaneous injection, intramuscular injection, intraperitoneal injection, dermal administration, etc., and most specifically, the pharmaceutical composition may be administered by a direct injection into the blood vessel (e.g., bolus injection or intravenous injection). Direct injection into the blood vessel means an administration into blood vessels, including arteries, veins, and capillaries, for example, main arteries, carotid arteries, subclavian arteries, celiac arteries, mesenteric arteries, renal arteries, iliac arteries, arterioles, capillaries, and venulas, and the administration manner may be selected appropriately according to the vascular portion in which the thrombus is generated.

In addition, the route of administration of the pharmaceutical composition of the present invention is preferably determined according to the disease type, to which the composition is applied, and the practitioner. For example, the concentration of the saxatilin derivative, which is an active ingredient contained in the composition of the present invention, may be determined considering the therapeutic purpose, the condition of the patient, the required period, or the like, and is not limited to a specific range of concentration. According to a certain embodiment of the present invention, the daily dose of the pharmaceutical composition of the present invention is 0.001-1,000 mg/kg.

The pharmaceutical composition of the present invention is formulated into a unit dosage form or in a multidose container, using a pharmaceutically acceptable carrier and/or excipient according to the method that can be easily conducted by a person having ordinary skills in the art to which the present invention pertains. Here, the dosage form may be a solution in an oily or aqueous medium, a suspension, an emulsion, an extract, a powder, a granule, a tablet, or a capsule, and may further include a dispersant or a stabilizer.

The pharmaceutical composition of the present invention is characterized in that the vascular stenosis or occlusive disease is treated not by the prevention or treatment through a simple principle of thrombus generation prevention, but by a principle in which the already generated thrombus is lysed to penetrate the blood vessel effectively. For example, in the case of stroke, the pharmaceutical composition (e.g., aspirin) that prevents thrombus generation has been already well known. However, once cerebral infarction occurs by thrombus generation and brain blood vessel occlusion, there are no pharmaceutical compositions that may effectively treat the cerebral infarction. The treatment by intravenous administration of recombinant tissue plasminogen activator (r-tPA) is currently the only approved therapy for cerebral infarction within 3 hours of symptom onset. However, the treatment using the plasminogen activator is constrained by time, and in a situation in which more than half of the patients fail to achieve successful recanalization after thrombolytic treatment, the present pharmaceutical composition, which can effectively lyse the already generated thrombi, is a very realistic and groundbreaking approach in the treatment of vascular stenosis or occlusive disease that has already occurred. Not only that, the pharmaceutical composition for vascular stenosis or occlusive disease of the present invention is of great value in that it effectively also treats microvascular occlusion and causes no restenosis.

In accordance with another aspect of the present invention, there is provided a method for preventing or treating vascular stenosis or occlusive disease, the method including administering a pharmaceutically effective amount of the saxatilin derivative to a subject.

In an embodiment of the present invention, the vascular stenosis or occlusive disease is selected from the group consisting of stroke, cerebral infarction, cerebral thrombosis, cerebral embolism, lacunar infarction, acute coronary syndrome, angina, aortic stenosis, myocardial infarction, migraine, bundle branch block, ischemia, acute ischemic arteriovascular event, thrombophlebitis, venous thromboembolism, deep vein thrombosis, pulmonary embolism, peripheral vascular disease, vascular headache, atherosclerosis, vascular spasm, restenosis, restenosis after balloon angioplasty, and vascular occlusion by vasculitis.

Since the method for the prevention or treatment of the present invention is achieved by administering to a subject the "saxatilin derivative" according to another aspect of the present invention, descriptions of overlapping contents between the two are omitted to avoid excessive complication of the specification due to repetitive descriptions thereof.

In accordance with another aspect of the present invention, there is provided a use of a saxatilin derivative for preventing or treating vascular stenosis or occlusive disease.

Since the use of the present invention is directed to the use of the "saxatilin derivative" according to another aspect of the present invention, descriptions of overlapping contents between the two are omitted to avoid excessive complication of the specification due to repetitive descriptions thereof.

Advantageous Effects

Features and advantages of the present invention are summarized as follows:

(a) The present invention relates to a saxatilin derivative having an increased half-life and a use thereof.

(b) The saxatilin derivative of the present invention has similar thrombolytic activity to the parent protein saxatilin as well as a significantly increased protein half-life, and enables very efficient lysis of the thrombi, which were already generated in the blood vessel in FeCl3-induced carotid artery animal models, using the saxatilin derivative.

(c) Therefore, the composition containing the saxatilin derivative as an active ingredient, of the present invention, causes no restenosis after canalization and effectively opens even microvessels, and thus the composition is very effective in the treatment of vascular stenosis or occlusive diseases (e.g., cerebrovascular diseases, cardiovascular diseases, arteriosclerotic vascular diseases, coronary artery diseases, and peripheral vascular diseases).

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Methods and Results

Construction, Expression, and Purification of Recombinant Saxatilin Protein Expression Vectors Construction of Fc-Saxatilin and Saxatilin-Fc Protein Expression Vectors For the expression of the recombinant saxatilin protein, the present inventors conducted PCR using the primer pair (saxatilin-F and saxatilin-R) shown in the table below. The obtained PCR products were cleaved with restriction enzyme sfiI (Thermo Scientific), and cloned into pYK603 vector and pYK602 vector (A&R Therapeutics) using T4 DNA ligase (Thermo Scientific), thereby constructing recombinant vectors for expressing Fc-saxatilin protein and saxatilin-Fc protein.

Primer sequences for expression vector of Fc-saxatilin (restriction enzyme cleavage sequences, underlined)

TABLE 1

Primer sequences for expression vector of Fc-saxatilin (restriction enzyme cleavage sequences, underlined)

| Primer name | sequence(5'→3') |
|---|---|
| saxatilin-F (SEQ ID NO: 8) | agta_ggccgtggaggcc_gaggccggagaagaatgtgactgt |
| saxatilin-R (SEQ ID NO: 9) | gcat_ggccgacgcggcc_aaggcatggaagggatttctgggaca |

Confirmation of Fc-Saxatilin and Saxatilin-Fc Protein Expression 292E cells were transfected with the foregoing recombinants vectors containing Fc-saxatilin and saxatilin-Fc using polyethylenimine (PEI, Polysciences), respectively. After the transfection, each supernatant was collected on day 2 or 5 of cell culture, subjected to SDS-PAGE, transferred to NC membrane (Millipore), and then allowed to react with a secondary antibody, anti-HuFc-HRP (1:2000 dilution, Thermo Scientific) at room temperature for 1 h. The NC membrane was washed three times with PBS/T, and then western blotting was conducted through ECL solution treatment and film development (FIG. 2).

Purification of Fc-Saxatilin and Saxatilin-Fc Proteins

On day 3, 5, or 7 of culture of the transfected 293E cells, each culture supernatant was filtered through 0.22-μm top-filter (Millipore). The filtered supernatant was loaded through 5 ml column packed with 500 μl of protein A beads (GE healthcare) to allow to bind with the beads. The binding reaction was conducted at 4° C. overnight at a flow rate of 0.9 ml/min using a peri-start pump (Bio-rad), followed by washing with 100 ml or more of PBS, and then six fractions were eluted using 0.1 M glycine-HCl. The eluates were neutralized with 1 M Tris (pH 9.0) solution. Thereafter, protein quantification was conducted, and the proteins contained in 2-3 fractions were concentrated using Amicon Ultra centrifugal filter (Millipore). Buffer was exchanged ten times or more with PBS.

The purity of the obtained protein concentrate was analyzed using Agilent 2100 bioanalyzer (FIGS. 3A and 3B). The Agilent 2100 bioanalyzer is a system that can automatically analyze both the size and concentration of proteins based on a lab-on-a-chip. The whole-processes of sample processing, isolating, and detecting, were simultaneously performed in microchips, thereby obtaining highly reliable data, of which the analysis results were then confirmed by two types (gel-electrophoretic imaging, and an electropherogram such as chromatography).

Platelet Aggregation-Inhibitory Activity of Fc-Saxatilin and Saxatilin-Fc Proteins Anesthetic solution was prepared by mixing zoletil 50 (VirBac) and rompun (Bayer) at a ratio of 3:1 and then 10-fold diluting the mixture with physiological saline. Female Institute of Cancer Research (ICR) mice (Orientbio Inc, Korea) were weighed, and 10 μl/g per g of the anesthetic solution was intraperitoneally injected. The anesthetized mouse was fixed and the abdomen part is cut open, and then the blood was collected and put in a sodium citrate tube (#363048; BD Science), followed by well stirring. The collected blood was transferred to a 15 ml tube, and centrifuged at 1,000 rpm for 15 minutes to obtain platelet-rich plasma (PRP). In addition, the lower hemocyte layer was again centrifuged at 3,000 rpm for 10-15 minutes to obtain supernatant (plasma). The supernatant (600 μl) was centrifuged at 10,000 rpm for 2 minutes to obtain hemocytes without platelet-poor plasma (PPP), and the remaining plasma was mixed with the PRP, which was separated in the previous step, before use. Platelet aggregation assay was conducted using an aggregometer (Model 700; Chrono-log). A first cuvette (#312; Chrono-log) added with PPP (500 μl), and a second cuvette added with PRP (480 μl) and saxatilin (10 μl) or recombinant saxatilin (Fc-saxatilin or saxatilin-Fc; 10 μl) were put in the aggregometer to set the baseline. Then, 10 μl of ADP (final concentration, 20 μM; #384; Chrono-log) was put in the second cuvette, followed by mixing through pipetting, and the aggregation degree was measured. Here, assuming that the aggregation degree was 100% for only ADP, on the basis of which the aggregation degree of each sample was calculated as a relative value. That is, the value obtained by subtracting the aggregation rate (%) of each sample from 100% was calculated as an inhibition (%). The $IC_{50}$ concentration of naturally occurring saxatilin with respect to platelet aggregation was 150 nM, and the $IC_{50}$ concentrations of Fc-saxatilin and saxatilin-Fc were 196 nM and 362 nM, respectively (FIG. 4), and these results show that the recombinant saxatilin of the present invention exhibited excellent platelet aggregation activity, which can be compared with that of saxatilin.

Half-Lives of Fc-Saxatilin and Saxatilin-Fc Proteins

N-hydroxysuccinimide-rhodamine (NHS-Rhodamine; #46406, 10 mg/ml; Thermo Scientific Pierce, USA) was added to reaction tubes containing saxatilin, Fc-saxatilin, and saxatilin-Fc (in PBS, pH 7.4), followed by a reaction at room temperature for 1 hour. Non-reacted NHS-Rhodamine was removed using PD10 salting column (#17-0851-01; GE Healthcare, USA). The concentrations of rhodamine-conjugated proteins were measured using BCA protein assay kit (#23225; Thermo Scientific Pierce, USA), and then the proteins were stored at 4° C. in dark conditions until used for experiments.

Rhodamine-labeled saxatilin was diluted with PBS buffer to 0.5 mg/ml, and then injected to 8-week aged ICR mice (three mice; Orientbio Inc, Korea) through the tail vein using an insulin injector (#32882; BD Science, USA). Here, the doses were 5 mg/10 ml/kg (mouse weight). The blood was collected from the jugular vein of the mice 0 min, 5 min, 10 min, 20 min, 40 min, and 80 min after the administration of the protein, and was maintained at room temperature in dark conditions for 30 min, leading to blood coagulation. The blood was centrifuged at 12,000 rpm for 10 min at 4° C. to separate supernatant (serum). 80 μl of the obtained serum was put in dark 96-well plate (#43711; Thermo Scientific Pierce, USA), and subjected to fluorescence measurement using a microplate fluorometer (excitation wavelength of 552 nm and emission wavelength of 575 nm; Thermo Scientific Pierce, USA), thereby calculating the half-life.

The rhodamine-conjugated Fc-saxatilin or saxatilin-Fc was diluted with PBS buffer to 0.5 mg/ml, and then injected to 9-week aged ICR mice (five mice) through the tail vein using an insulin injector. Here, the doses were 5 mg/10 ml/kg (mouse weight). The blood was collected from the jugular vein of the mice 0 min, 5 min, 10 min, 20 min, 30 min, 60 min, 2 hr, 4 h, and 8 h after the administration of the protein, and was maintained at room temperature in dark conditions for 30 min, leading to blood coagulation. The blood was centrifuged at 12,000 rpm for 10 min at 4° C. to separate supernatant (serum). 80 μl of the obtained serum was put in dark 96-well plate (#43711; Thermo Scientific Pierce, USA), and subjected to fluorescence measurement using a microplate fluorometer (excitation wavelength of 552 nm and emission wavelength of 575 nm), thereby calculating the half-life.

Figure 1:
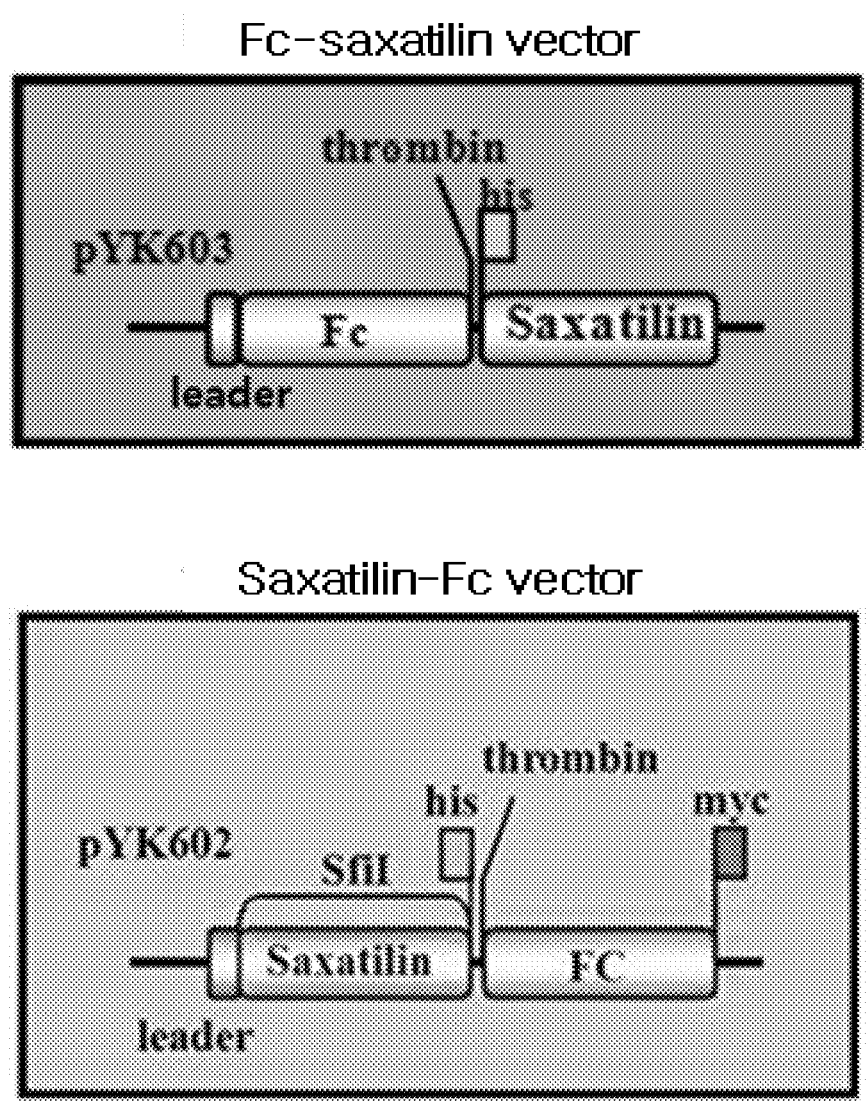
FIG. 1 schematically shows structures of saxatilin derivatives that are cloned to multicloning sites of pYK603 vector and pYK602 vector, respectively. The distance between components or the distance between restriction enzymes is not drawn to the scale. leader (leader sequence), immunoglobulin G2a gamma chain.
Figure 2:
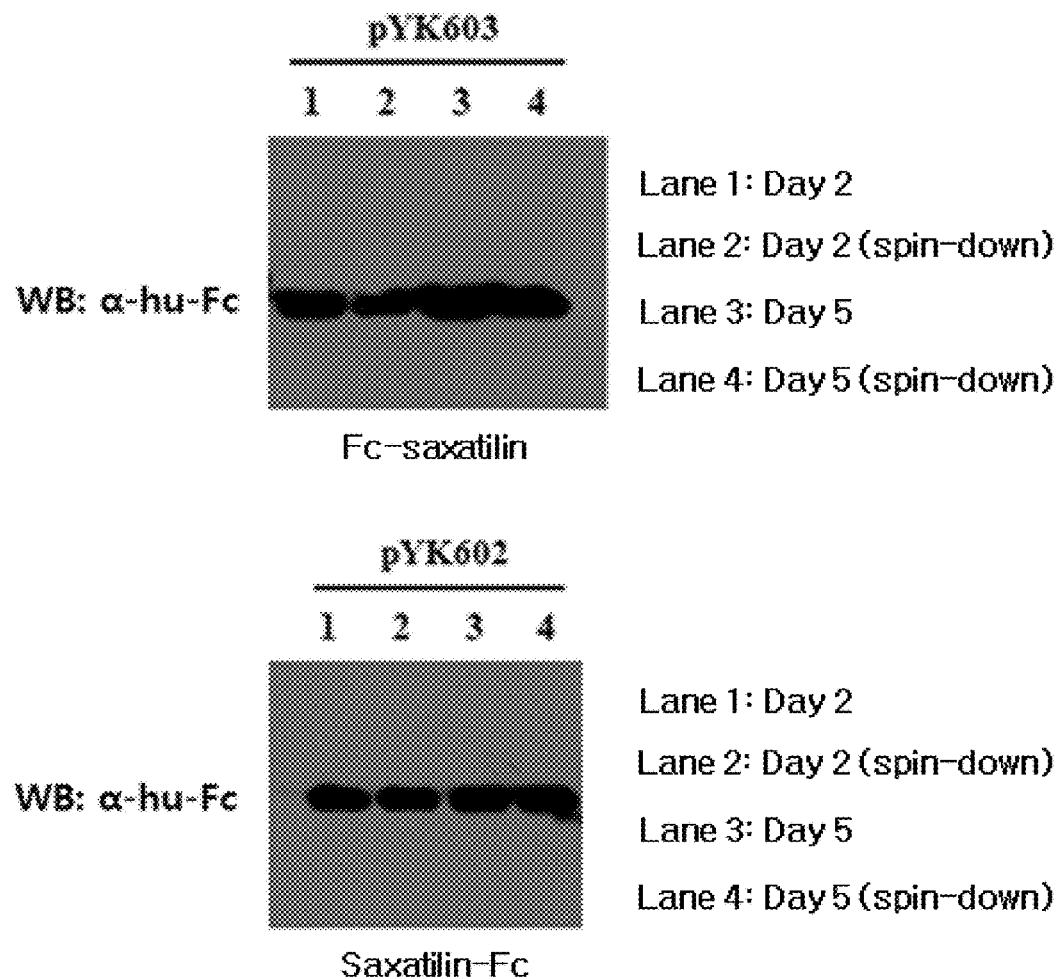
FIG. 2 shows western blotting results confirming the expression of the saxatilin derivatives of the present invention. For verifying the stability of purified proteins, the presence or absence of precipitates was checked by centrifugation at 5,000 rpm for 10 minutes (lane 2 and lane 4). As a result, the saxatilin derivatives of the present invention were very stable (no precipitations).
Figure 3A:
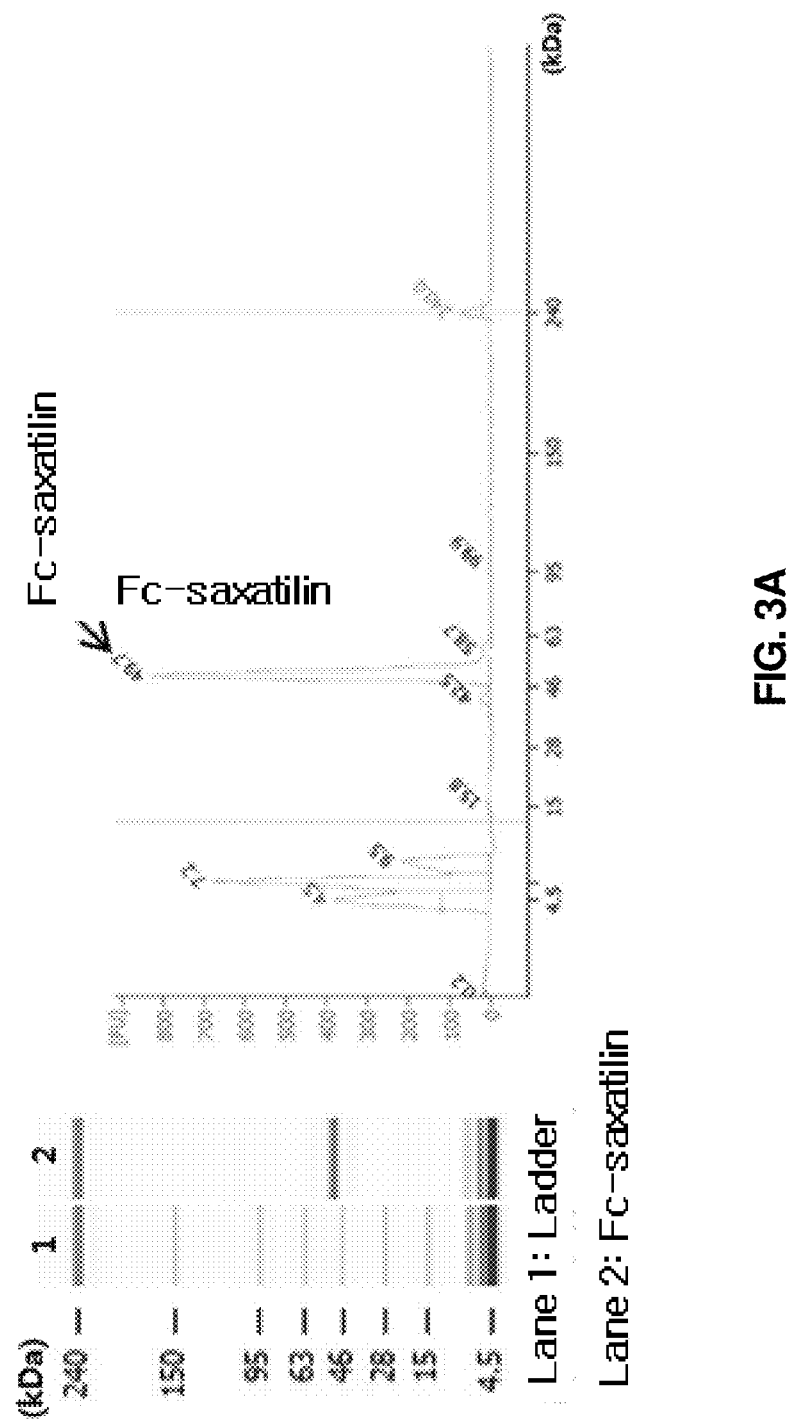
FIGS. 3A and 3B show purification results of Fc-saxatilin and saxatilin-Fc, respectively. Gel-electrophoresis images (left panels) and electropherograms (right panels) are presented.
Figure 3B:
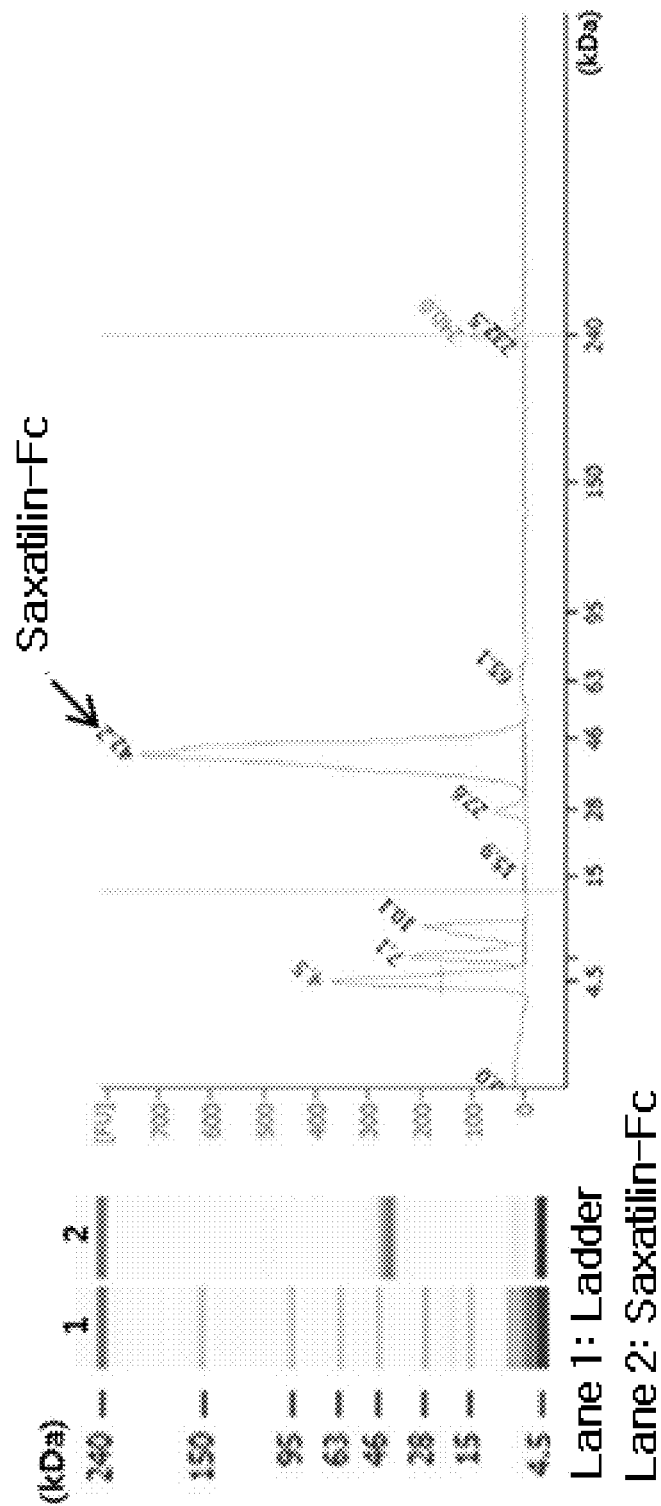
Figure 4:
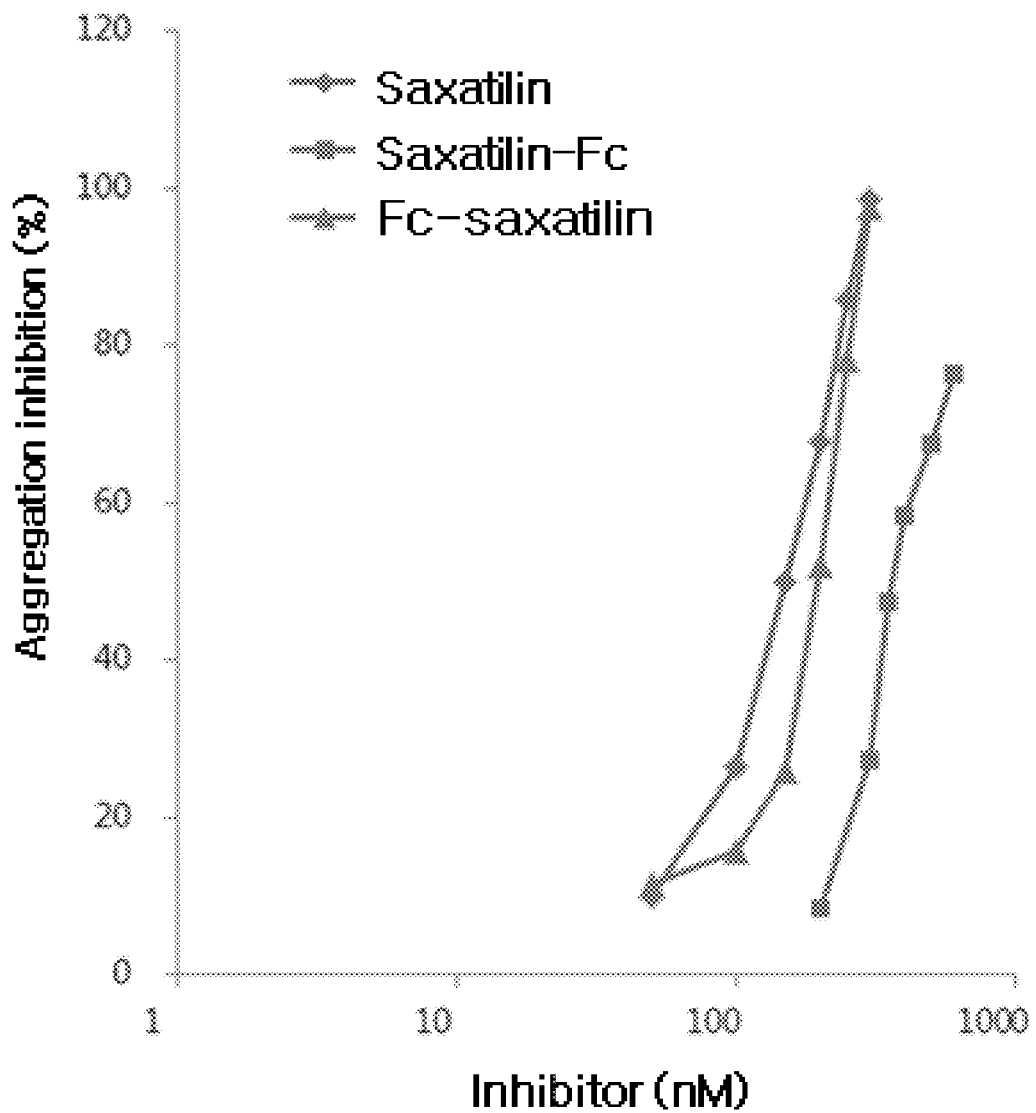
FIG. 4 shows measurement results of platelets aggregation-inhibitory activities of saxatilin, as a parent protein, and the saxatilin derivatives of the present invention (Fc-saxatilin and saxatilin-Fc). For platelet aggregation assay, saxatilin, as a parent protein, and Fc-saxatilin were used at 100, 150, 200, 250, and 300 nM, and saxatilin-Fc was used at 200, 300, 350, 400, 500, and 600 nM.
Figure 5A:
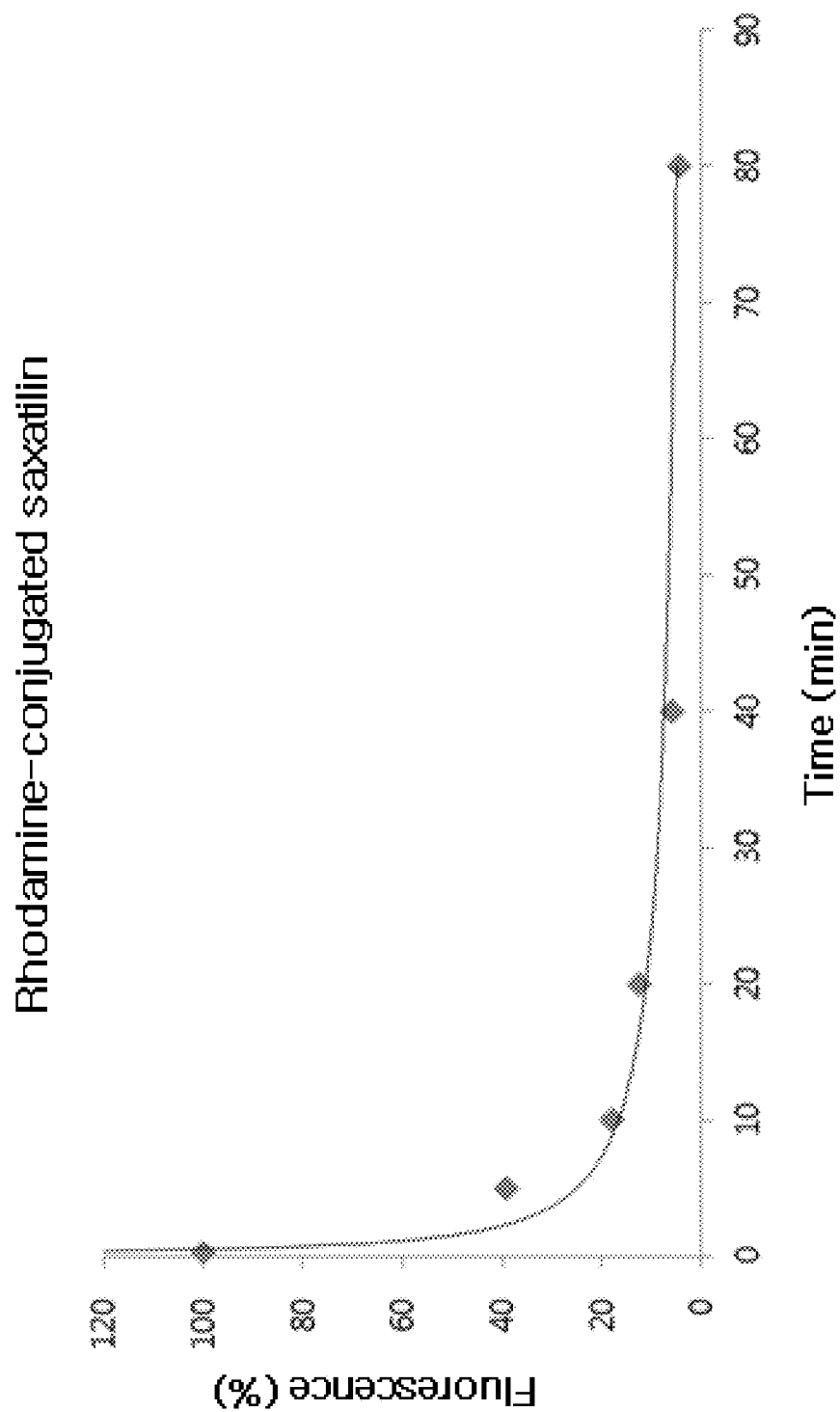
FIGS. 5A, 5B and 5C shows measurement results of half-lives of saxatilin, as a parent protein, and the saxatilin derivatives (Fc-saxatilin and saxatilin-Fc) of the present invention.
Figure 5B:
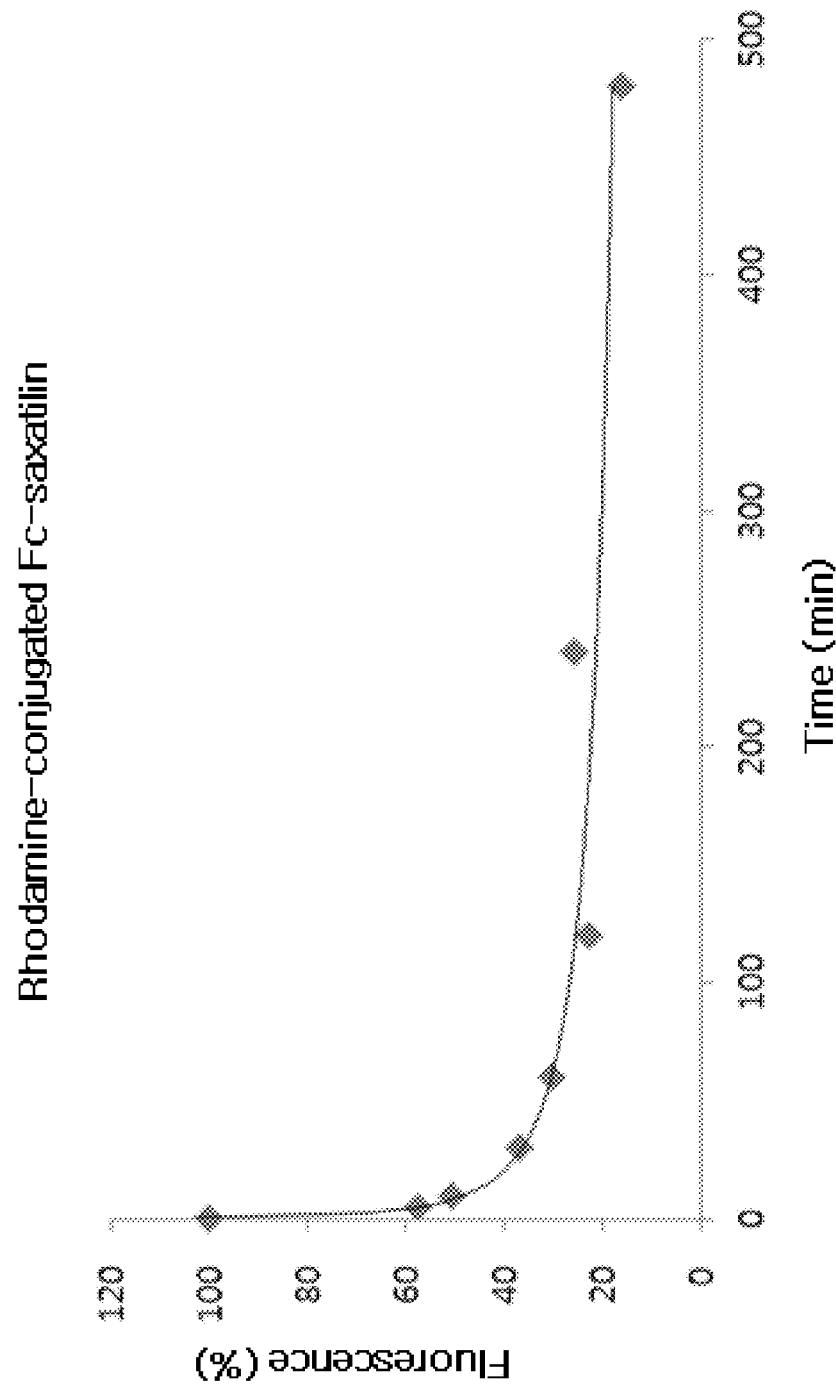
Figure 5C:
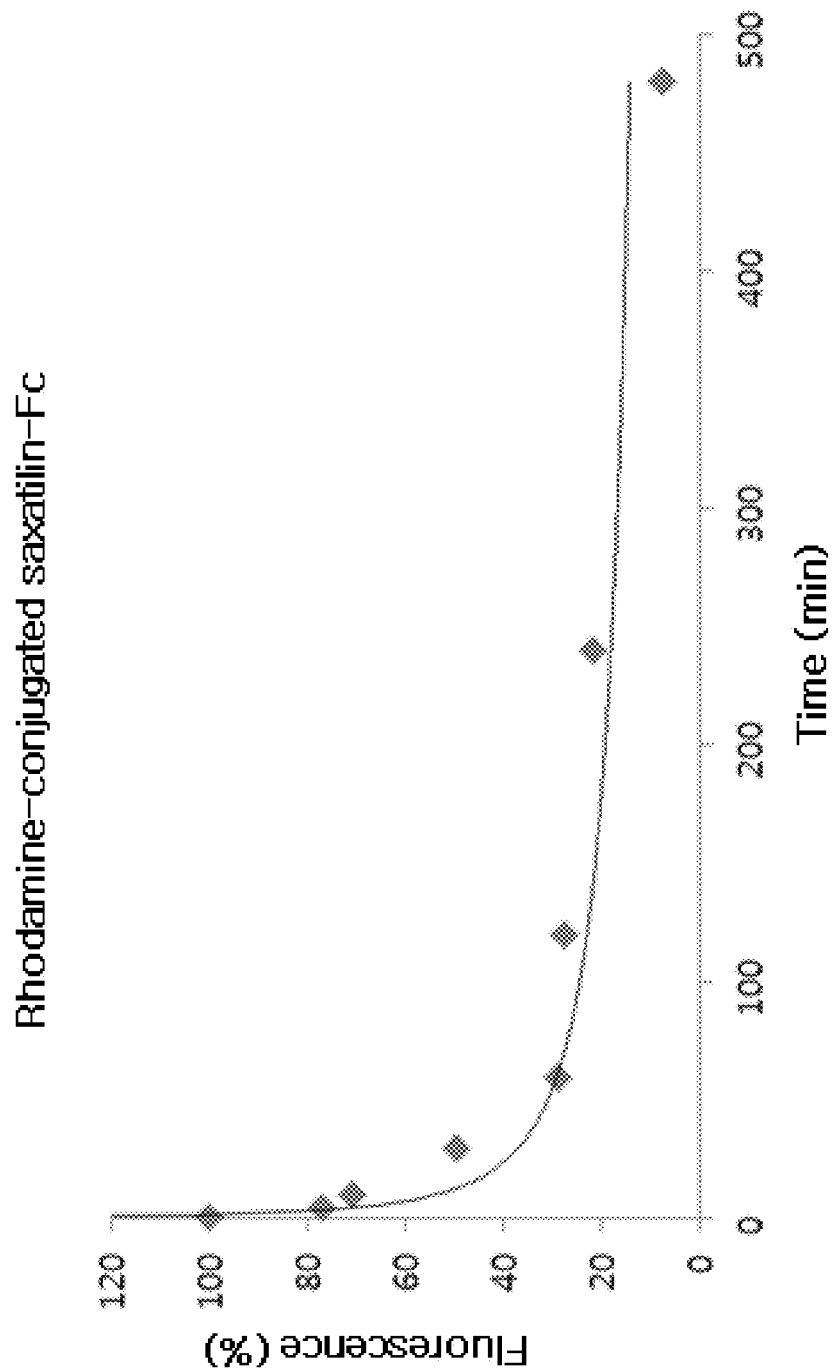
Figure 6:
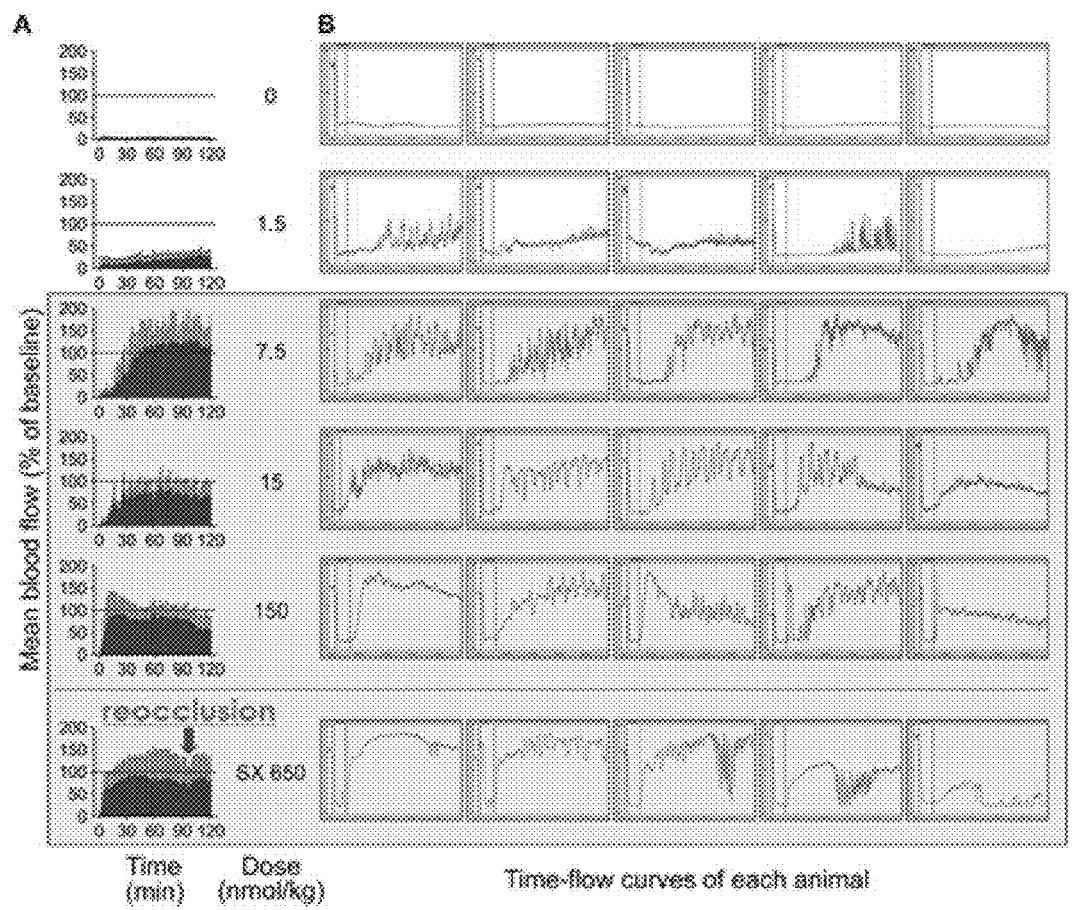
FIG. 6 shows thrombolytic effect comparison results between the saxatilin derivative and 650 nmol/kg saxatilin. In addition, the presence and degree of recanalization were determined by measuring the blood flow.

As a result, the half-lives of the rhodamine-conjugated saxatilin, Fc-saxatilin, and saxatilin-Fc were 2.0 min, 8.6 min, and 12.5 min, respectively (FIGS. 5A to 5C). Therefore, it was confirmed that the Fc-saxatilin and saxatilin-Fc of the present invention had significantly increased half-lives compared with saxatilin.

Binding Between Integrin and Saxatilin

Integrins ($\alpha_{IIb}\beta_3$, $\alpha_v\beta_3$, $\alpha_M\beta_2$, and $\alpha_L\beta_2$) were added to 96-well plate at 100 ng/well, respectively, followed by coating at 4° C. overnight. After the coating, the wells were washed three times with PBS-T (0.5% Tween 20). The wells were blocked with 1% BSA (in PBS-T) solution at room temperature for 2 h. After the blocking, the wells were washed three times with PBS-T. Saxatilin-Fc or Fc-saxatilin was diluted serially 4-fold from 100 nM to prepare eight sample solutions.

100 µl of the sample solutions were triply loaded to each well, followed by a reaction at room temperature for 2 h. After the reaction, the wells were washed three times with PBS-T. 100 µl of anti-human IgG (Fc)-conjugated HRP antibodies, diluted to 1:20,000, was added to each well, followed by a reaction at room temperature for 1 h. After the reaction, the wells were washed four times with PBS-T. TMB solution was added, followed by a reaction at room temperature for 30 min, and then the reaction was stopped by adding a stop solution (0.5 M $H_2SO_4$). The absorbance was measured at 450 nm to verify the binding between saxatilin and integrins, involved in an interaction between neutrophils and endothelial cells.

Figure 9:
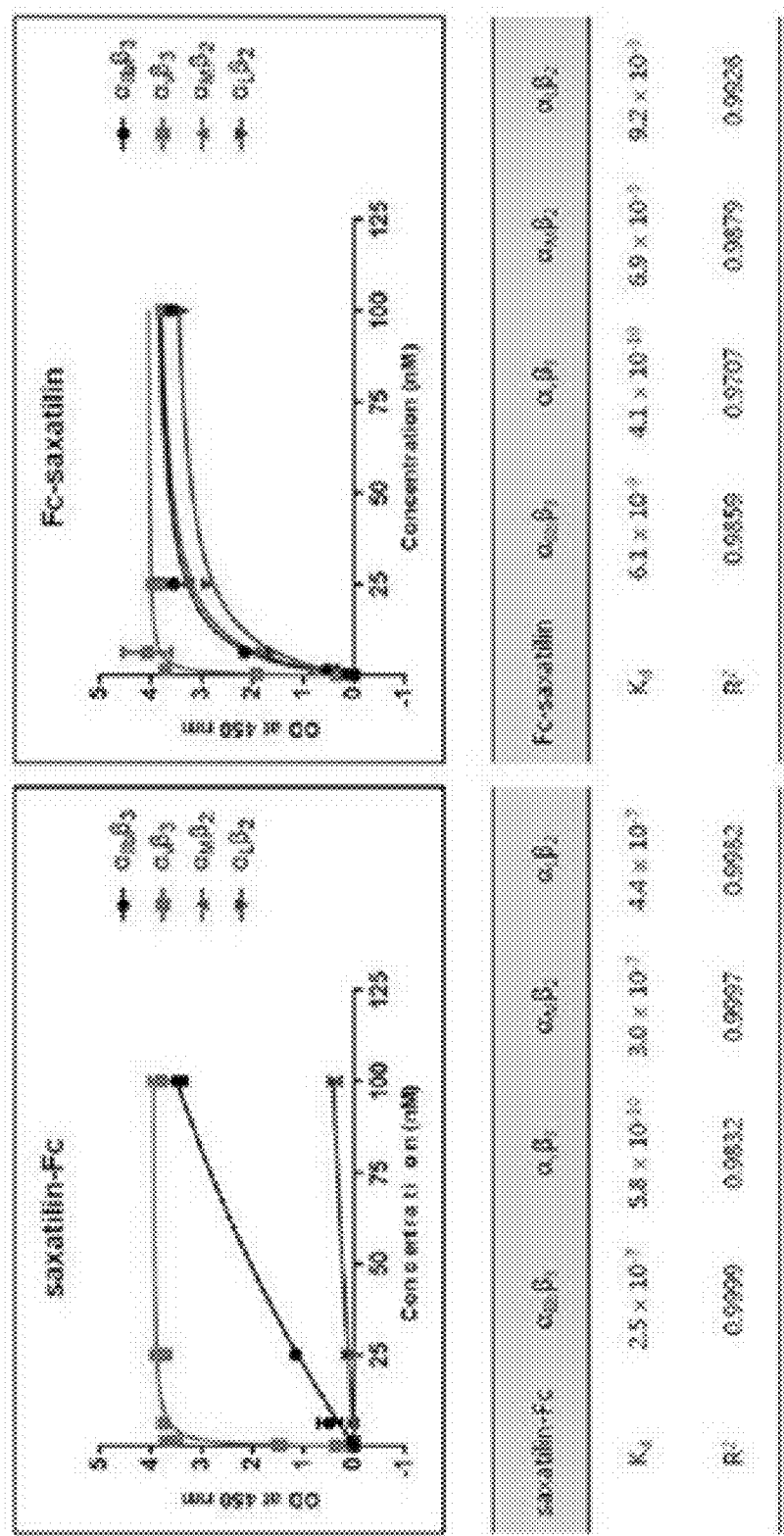
FIG. 9 shows the binding between Integrins ($\alpha_{IIb}\beta_3$, $\alpha_v\beta_3$, $\alpha_M\beta_2$, and $\alpha_L\beta_2$) and Saxatilin derivatives.

Integrins $\alpha_M\beta_2$ and $\alpha_L\beta_2$, which exist in the neutrophils, interact with intercellular adhesion molecule 1 (ICAM-1) in endothelial cells to allow the neutrophils to gather in the endothelial cells. As a result of binding analysis using ELISA, Fc-saxatilin strongly bound with integrins $\alpha_M\beta_2$ and $\alpha_L\beta_2$ (Kd, $6.9\times10^{-9}$ M and $9.2\times10^{-9}$M). In addition, although more weakly than Fc-saxatilin, the saxatilin-Fc bound with integrins $\alpha_M\beta_2$ and $\alpha_L\beta_2$ (Kd, $3.0\times10^{-7}$ M and $4.4\times10^{-7}$ M) (FIG. 9).

Thrombolytic Effect of Recombinant Saxatilin Derivatives Using Thrombolysis Model by $FeCl_3$ 8-week aged female ICR mice with 32-34 g were used. Animal care and use were performed according to protocols reviewed and approved by the Institutional Animal Care and Use Committee (IACUC) at the Yonsei University College of Medicine on the basis of the standards suitable to the guide of the Association for Assessment and Accreditation of Laboratory Animal Care, International (AAALAC). For surgical operation, animals were anesthetized through breathing with 5% isoflurane in a mixture (Hankook Special Gases, Korea) composed of 70% $N_2O$ and 30% $O_2$. The anesthetization was maintained with 2% isoflurane. During the surgical operation, the animal body temperature was continuously monitored using a probe, and maintained at 37.0±0.2° C. using a homeothermic blanket control unit and heating pad (Harvard Apparatus, Holliston, Mass.). In order to test in vivo thrombolytic activity of saxatilin and saxatilin-Fc, $FeCl_3$ (Sigma-Aldrich, USA)-induced carotid artery thrombus models were used. A midline cervical incision was made to carefully anatomize the common carotid artery (CCA) under an operating microscope (SEILER, USA). An ultrasonic doppler flow probe (Transonic MA0.7PSB) was positioned at the center portion of the common carotid artery (CCA). The carotid blood flow was measured using an ultrasonic TS420 blood flowmeter (Transonic Instruments, Ithaca, N.Y.) and an iWorx IX-304T data acquisition system (iWorx Systems, Inc., Dover, N.H.). The baseline blood flow of CCA was measured for 5 min for a control. After the determination of the baseline blood flow of the control, the probe was removed. Oxidative vascular injury by chemical stress was induced by placing a filter paper (700×500 µm) saturated with 50% $FeCl_3$ on the adventitial surface of the midpoint of the exposed CCA for 5 min. After removing the filter paper, the CCA was washed with physiological saline, and the blood flow thereof was measured. Thrombus generation and arterial occlusion were determined by a decrease in the blood flow, and the complete occlusion was defined as an absence of the blood flow for 10 minutes.

Ten minutes after occlusion of the CCA, Fc-saxatilin was bolus-injected at 0, 1.5, 7.5, 15, and 150 nmol/kg through the left femoral vein by using an infusion pump (KD Scientific Inc., USA) connected to PE-10 tubing (Becton Dickinson and Company, USA). The carotid blood flow was continuously monitored for 2 hours from the initial time of injection. The thrombolytic effect was evaluated using five mice per group, and compared with the effect of 650 nmol/kg saxatilin, which was evaluated in a previous study.

Figure 7:
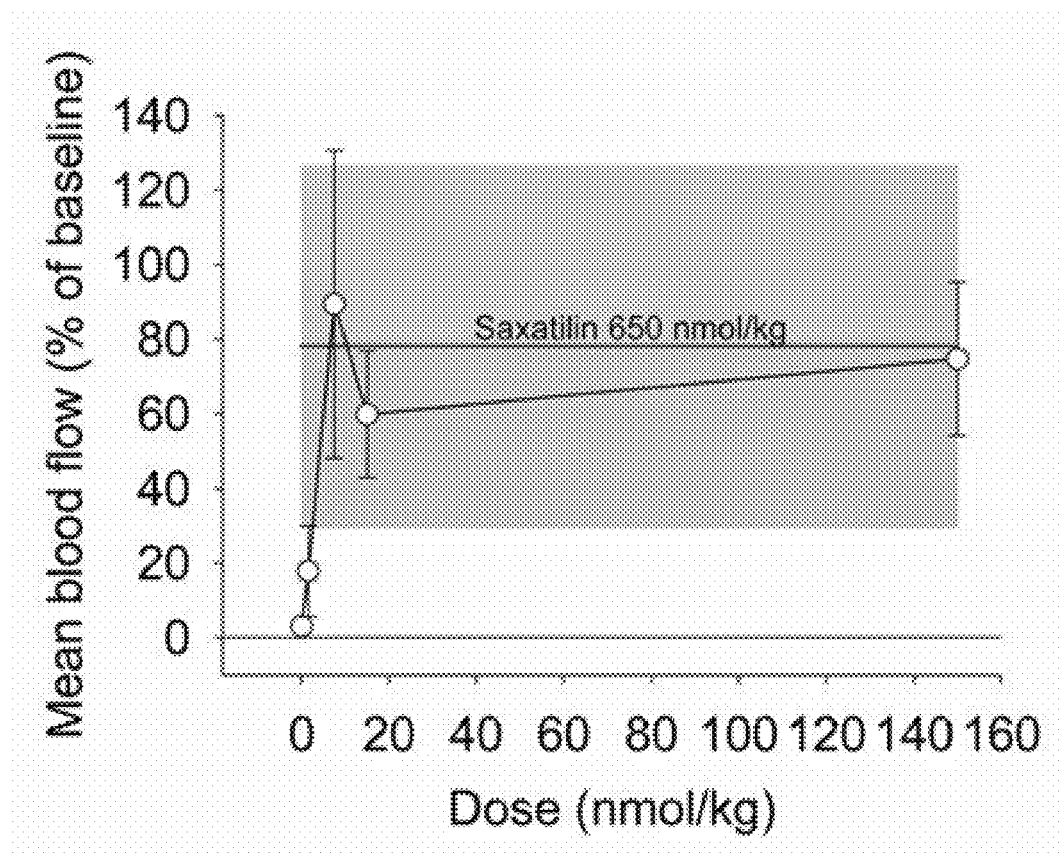
FIG. 7 shows a dose-response curve of the mean values of each group that were obtained in a dose-response study. It shows comparison results with the thrombolytic effects of 650 nmol/kg saxatilin (mean; red line; standard deviation; red area), which were obtained in the previous study.

In addition, the presence and degree of recanalization were determined by measuring the blood flow. Data about the baseline blood flow and the blood flow monitored continuously for 2 h after CCA occlusion were obtained using iWorx Labscribe2 data acquisition software (version 2.045000). The carotid blood flow was analyzed by calculating the area under the obtained flow-time curve. All the measured values were standardized by the minimum blood flow of each animal to avoid differences caused by the variation in physiological condition between animals. The thrombolytic effect was calculated as below, and expressed as a percent of mean baseline blood flow: (mean blood flow for 2 h after saxatilin derivative administration/mean baseline blood flow)×100(%). In dose-response study, the mean values of each group were calculated and expressed by a dose-response curve (mean±SD, FIG. 7). In addition, the above results were compared with the thrombolytic effects (mean; red line; standard deviation; red region) of 650 nmol/kg saxatilin, which was obtained in the previous study). Meanwhile, the mean blood flow of every 1 min was calculated in each animal, and respective representative patterns of dose and administration method were checked in a dose-dependent manner. The mean values of all animals in the respective group were calculated, and the temporal changes were shown through continuous bar graphs (mean±SD).

When compared with the baseline blood flow, the mean percents of blood flow in administration groups were as follows (FIG. 7): (a) physiological saline administered group, 3.03±0.75%; (b) Fc-saxatilin 1.5 nmol/kg administered group, 17.81±12.22%; (c) Fc-saxatilin 7.5 nmol/kg administered group, 89.40±41.18%; (d) Fc-saxatilin 15 nmol/kg administered group, 59.94±16.97%; (e) Fc-saxatilin 150 nmol/kg administered group, 74.68±20.53%; and (f) saxatilin 650 nmol/kg administered group, 78.24±48.61% (mean±SD).

Figure 8:
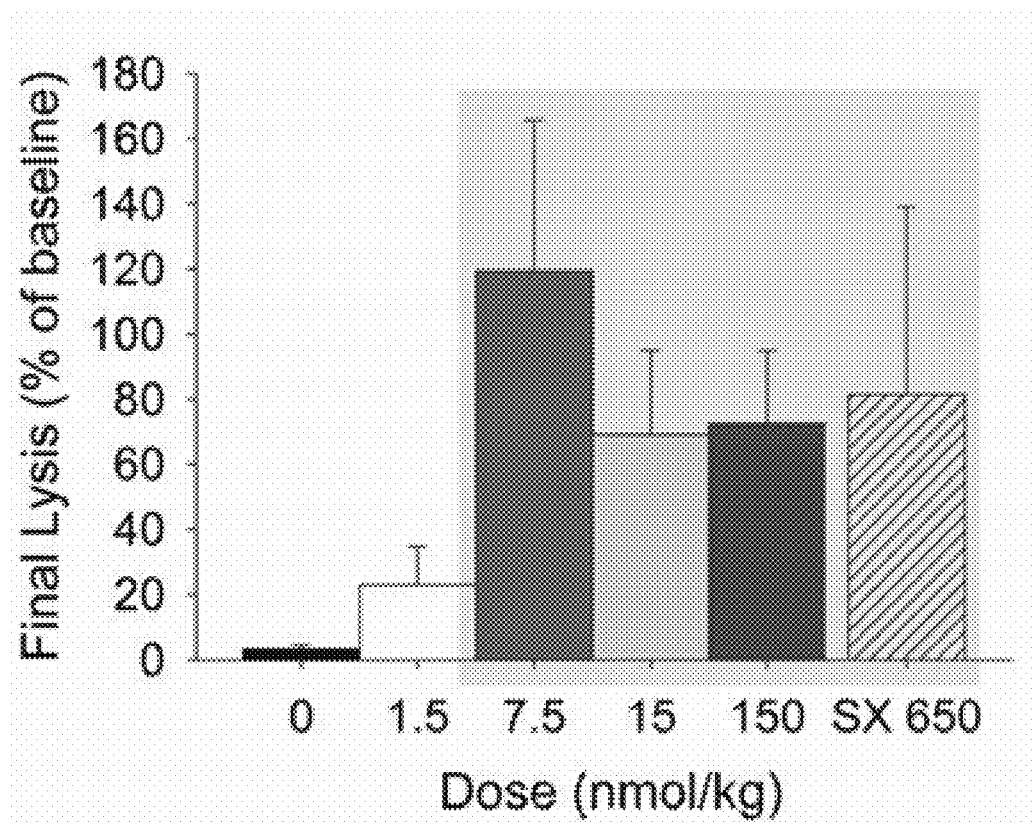
FIG. 8 shows the mean blood flow percent to the baseline blood flow, for the last 10 minutes of 2 hours of the measurement of thrombolytic effect.

The mean blood flow percent to the baseline blood flow, for the last 10 minutes of 2 hours of the measurement of thrombolytic effect, was analyzed (FIG. 8). (a) physiological saline administered group, 3.29±1.25%; (b) Fc-saxatilin 1.5 nmol/kg administered group, 23.06±11.75%; (c) Fc-saxatilin 7.5 nmol/kg administered group, 119.52±46.32%; (d) Fc-saxatilin 15 nmol/kg administered group, 69.05±26.07%; (e) Fc-saxatilin 150 nmol/kg administered group, 72.49±22.49%; and (f) Fc-saxatilin 650 nmol/kg administered group, 81.54±57.50% (mean±SD).

In summary, Fc-saxatilin showed a dose-dependent thrombolytic effect. The mean thrombolytic effect and the thrombolytic effect for last 10 minutes by Fc-saxatilin 7.5 nmol/kg, 15 nmol/kg, and 150 nmol/kg administration showed statistically similar effects compared with existing saxatilin 650 nmol/kg.

In the case where 650 nmol/kg saxatilin was administered, the saxatilin administered group showed clear decreases in the thrombolytic effect and the thrombus reformation inhibitory effect with the passage of time. The above-described abrupt reocclusion was observed in three of a total of five mice, into which saxatilin was bolus-injected, for above 90 minutes on average. Whereas, it was confirmed that, in cases where Fc-saxatilin was administered in 7.5 nmol/kg or more, the thrombolytic effect and the thrombus formation inhibitory effect were constantly maintained for 2 hours without reocclusion after recanalization.

Although the present invention has been described in detail with reference to the specific features, it will be apparent to those skilled in the art that this description is only for a certain embodiment and does not limit the scope of the present invention. Thus, the substantial scope of the present invention will be defined by the appended claims and equivalents thereof.

REFERENCES 1. (1995). "Tissue plasminogen activator for acute ischemic stroke. The National Institute of Neurological Disorders and Stroke rt-PA Stroke Study Group." N Engl J Med 333(24): 1581-1587.
2. Abou-Chebl, A., C. T. Bajzer, et al. (2005). "Multimodal therapy for the treatment of severe ischemic stroke combining GPIIb/IIIa antagonists and angioplasty after failure of thrombolysis." Stroke 36(10): 2286-2288.
3. Abumiya, T., R. Fitridge, et al. (2000). "Integrin alpha (IIb)beta(3) inhibitor preserves microvascular patency in experimental acute focal cerebral ischemia." Stroke 31(6): 1402-1409; discussion 1409-1410.
4. Adams, H., R. Adams, et al. (2005). "Guidelines for the early management of patients with ischemic stroke: 2005 guidelines update a scientific statement from the Stroke Council of the American Heart Association/American Stroke Association." Stroke 36(4): 916-923.
5. Adams, H. P., Jr., M. B. Effron, et al. (2008). "Emergency administration of abciximab for treatment of patients with acute ischemic stroke: results of an international phase III trial: Abciximab in Emergency Treatment of Stroke Trial (AbESTT-II)." Stroke 39(1): 87-99.
6. Alexandrov, A. V. and J. C. Grotta (2002). "Arterial reocclusion in stroke patients treated with intravenous tissue plasminogen activator." Neurology 59(6): 862-867.
7. Caplan, L. R., J. P. Mohr, et al. (1997). "Should thrombolytic therapy be the first-line treatment for acute ischemic stroke? Thrombolysis—not a panacea for ischemic stroke." N Engl J Med 337(18): 1309-1310; discussion 1313.
8. Chen, H., W. Mo, et al. (2007). "Characterization of a novel bifunctional mutant of staphylokinase with platelet-targeted thrombolysis and antiplatelet aggregation activities." BMC Mol Biol 8: 88.
9. Chen, Z. L. and S. Strickland (1997). "Neuronal death in the hippocampus is promoted by plasmin-catalyzed degradation of laminin." Cell 91(7): 917-925.
10. Choi, J. H., B. T. Bateman, et al. (2006). "Endovascular recanalization therapy in acute ischemic stroke." Stroke 37(2): 419-424.
11. Choudhri, T. F., B. L. Hoh, et al. (1998). "Reduced microvascular thrombosis and improved outcome in acute murine stroke by inhibiting GP IIb/IIIa receptor-mediated platelet aggregation." J Clin Invest 102(7): 1301-1310.
12. Ciccone, A., I. Abraha, et al. (2007). "Glycoprotein IIb-IIIa Inhibitors for Acute Ischemic Stroke." Stroke.
13. Eckert, B., C. Koch, et al. (2005). "Aggressive therapy with intravenous abciximab and intra-arterial rtPA and additional PTA/stenting improves clinical outcome in acute vertebrobasilar occlusion: combined local fibrinolysis and intravenous abciximab in acute vertebrobasilar stroke treatment (FAST): results of a multicenter study." Stroke 36(6): 1160-1165.
14. Hallenbeck, J. M. and A. J. Dutka (1990). "Background review and current concepts of reperfusion injury." Arch Neurol 47(11): 1245-1254.
15. Heo, J. H., K. Y. Lee, et al. (2003). "Immediate reocclusion following a successful thrombolysis in acute stroke: a pilot study." Neurology 60(10): 1684-1687.
16. Hong, S. Y., Y. S. Koh, et al. (2002). "Snake venom disintegrin, saxatilin, inhibits platelet aggregation, human umbilical vein endothelial cell proliferation, and smooth muscle cell migration." Thromb Res 105(1): 79-86.
17. Hong, S. Y., Y. D. Sohn, et al. (2002). "Structural and functional significance of disulfide bonds in saxatilin, a 7.7 kDa disintegrin." Biochem Biophys Res Commun 293(1): 530-536.
18. Hussain, M. S., R. Lin, et al. (2010). "Symptomatic delayed reocclusion after initial successful revascularization in acute ischemic stroke." J Stroke Cerebrovasc Dis 19(1): 36-39.
19. Jang, Y. J., 0. H. Jeon, et al. (2007). "Saxatilin, a snake venom disintegrin, regulates platelet activation associated with human vascular endothelial cell migration and invasion." J Vasc Res 44(2): 129-137.
20. Konstantinides, S., K. Schafer, et al. (2001). "Plasminogen activator inhibitor-1 and its cofactor vitronectin stabilize arterial thrombi after vascular injury in mice." Circulation 103(4): 576-583.
21. Kurz, K. D., B. W. Main, et al. (1990). "Rat model of arterial thrombosis induced by ferric chloride." Thromb Res 60(4): 269-280.
22. Lopez-Yunez, A. M., A. Bruno, et al. (2001). "Protocol violations in community-based rTPA stroke treatment are associated with symptomatic intracerebral hemorrhage." Stroke 32(1): 12-16.
23. Matys, T. and S. Strickland (2003). "Tissue plasminogen activator and NMDA receptor cleavage." Nat Med 9(4): 371-372; author reply 372-373.
24. Nicole, O., F. Docagne, et al. (2001). "The proteolytic activity of tissue-plasminogen activator enhances NMDA receptor-mediated signaling." Nat Med 7(1): 59-64.
25. Phillips, D. R., I. F. Charo, et al. (1988). "The platelet membrane glycoprotein IIb-IIIa complex." Blood 71(4): 831-843.
26. Qureshi, A. I., A. M. Siddiqui, et al. (2004). "Reocclusion of recanalized arteries during intra-arterial thrombolysis for acute ischemic stroke." AJNR Am J Neuroradiol 25(2): 322-328.
27. Rha, J. H. and J. L. Saver (2007). "The impact of recanalization on ischemic stroke outcome: a meta-analysis." Stroke 38(3): 967-973.

28. Seitz, R. J., M. Hamzavi, et al. (2003). "Thrombolysis with recombinant tissue plasminogen activator and tirofiban in stroke: preliminary observations." Stroke 34(8): 1932-1935.
29. Seitz, R. J., S. Meisel, et al. (2004). "The effect of combined thrombolysis with rtPA and tirofiban on ischemic brain lesions." Neurology 62(11): 2110-2112.
30. Shattil, S. J. and M. H. Ginsberg (1997). "Integrin signaling in vascular biology." J Clin Invest 100(11 Suppl): S91-95.
31. Sohn, Y. D., S. Y. Hong, et al. (2008). "Acute and repeated dose toxicity studies of recombinant saxatilin, a disintegrin from the Korean snake (*Gloydius saxatilis*)." Toxicon 51(3): 406-417.
32. Wang, Y. F., S. E. Tsirka, et al. (1998). "Tissue plasminogen activator (tPA) increases neuronal damage after focal cerebral ischemia in wild-type and tPA-deficient mice." Nat Med 4(2): 228-231.
33. Wardlaw, J. M., V. Murray, et al. (2009). "Thrombolysis for acute ischaemic stroke." Cochrane Database Syst Rev(4): CD000213.
34. Yepes, M., M. Sandkvist, et al. (2002). "Regulation of seizure spreading by neuroserpin and tissue-type plasminogen activator is plasminogen-independent." J Clin Invest 109(12): 1571-1578.

What is claimed is:

1. A method for treating vascular stenosis or occlusive disease due to thrombi, comprising:
   administering to a subject in need thereof a pharmaceutically effective amount of a saxatilin derivative comprising saxatilin, which consists of the amino acid sequence of SEQ ID NO: 2, conjugated to an immunoglobulin Fc region.

2. The method of claim 1, wherein a blood vessel involved in the vascular stenosis is main arteries, carotid arteries, subclavian arteries, celiac arteries, mesenteric arteries, renal arteries, iliac arteries, arterioles, capillaries, or venulas.

3. The method of claim 1, wherein the saxatilin derivative comprises a leader sequence further conjugated to the N-terminal.

4. The method of claim 1, wherein the vascular stenosis or occlusive disease is selected from the group consisting of stroke, cerebral infarction, cerebral thrombosis, cerebral embolism, lacunar infarction, acute coronary syndrome, angina, aortic stenosis, myocardial infarction, migraine, bundle branch block, ischemia, acute ischemic arteriovascular event, thrombophlebitis, venous thromboembolism, deep vein thrombosis, pulmonary embolism, peripheral vascular disease, vascular headache, atherosclerosis, vascular spasm, restenosis, restenosis after balloon angioplasty, and vascular occlusion by vasculitis.

5. The method of claim 1, wherein the immunoglobulin Fc region is conjugated to the N-terminal or C-terminal of the saxatilin.

6. The method of claim 1, wherein the saxatilin derivative has a half-life, which is increased by 4- to 6.5-fold when compared with naturally occurring saxatilin.

7. The method of claim 1, wherein the saxatilin derivative has a similar thrombolytic ability to naturally occurring saxatilin.

8. The method of claim 1, wherein the saxatilin derivative has an $IC_{50}$ value of 100-500 nM with respect to platelet aggregation.

9. The method of claim 1, wherein the saxatilin derivative binds to integrins existing in a thrombus to break up the thrombus.

10. The method of claim 1, wherein the saxatilin derivative binds to glycoprotein (GP) IIb-IIIa on the surface of platelets constituting the thrombus to break up the thrombus.

11. The method of claim 1, wherein the saxatilin derivative has a binding affinity (dissociation constant (Kd)) of $1 \times 10^{-8}$ to $1 \times 10^{-10}$ M to integrin $\alpha_M \beta 2$ existing in neutrophils.

12. The method of claim 1, wherein the saxatilin derivative has a binding affinity (dissociation constant (Kd)) of $1 \times 10^{-8}$ to $1 \times 10^{-10}$ M to integrin $\alpha_L \beta 2$ existing in neutrophils.

13. The method of claim 1, wherein the pharmaceutically effective amount of the saxatilin derivative is administered through a direct injection into the blood vessel.

\* \* \* \* \*